(12) United States Patent
Cao et al.

(10) Patent No.: US 8,317,783 B2
(45) Date of Patent: Nov. 27, 2012

(54) ASSESSMENT OF ELECTRODE COUPLING FOR TISSUE ABLATION

(75) Inventors: Hong Cao, Savage, MN (US); Saurav Paul, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1120 days.

(21) Appl. No.: 12/095,686

(22) PCT Filed: Dec. 6, 2006

(86) PCT No.: PCT/US2006/061713
§ 371 (c)(1),
(2), (4) Date: May 30, 2008

(87) PCT Pub. No.: WO2007/067940
PCT Pub. Date: Jun. 14, 2007

(65) Prior Publication Data
US 2010/0298823 A1   Nov. 25, 2010

Related U.S. Application Data

(60) Provisional application No. 60/748,234, filed on Dec. 6, 2005, provisional application No. 60/829,297, filed on Oct. 12, 2006.

(51) Int. Cl.
*A61B 18/04* (2006.01)
*A61B 5/05* (2006.01)
(52) U.S. Cl. .............. 606/34; 606/35; 600/547
(58) Field of Classification Search .......... 600/547; 606/35
See application file for complete search history.

(56) References Cited

U.S. PATENT DOCUMENTS

| | | | |
|---|---|---|---|
| 5,230,349 A | 7/1993 | Langberg |
| 5,257,635 A | 11/1993 | Langberg |
| 5,341,807 A | 8/1994 | Nardella |
| 5,447,529 A | 9/1995 | Marchlinski et al. |
| 5,582,609 A | 12/1996 | Swanson et al. |

(Continued)

FOREIGN PATENT DOCUMENTS
EP         1472976        11/2004
(Continued)

OTHER PUBLICATIONS

Avitall Boaz et al., "The Effects of Electrode-Tissue Contact on Radiofrequency Lesion Generation", *PACE*, vol. 20 Dec. 1997, 2899-2910.

*Primary Examiner* — Linda C Dvorak
*Assistant Examiner* — Jaymi Della
(74) *Attorney, Agent, or Firm* — Marsh Fischmann & Breyfogle LLP

(57) ABSTRACT

An electrode catheter and a method for assessing electrode-tissue contact and coupling are disclosed. An exemplary electrode catheter comprises an electrode adapted to apply electrical energy. A measurement circuit is adapted to measure impedance between the electrode and ground as the electrode approaches a target tissue. A processor determines a contact and coupling condition for the target tissue based at least in part on reactance of the impedance measured by the measurement circuit. In another exemplary embodiment, the electrode catheter determines the contact and coupling condition based at least in part on a phase angle of the impedance.

7 Claims, 19 Drawing Sheets

U.S. PATENT DOCUMENTS

| | | | |
|---|---|---|---|
| 5,588,432 A | 12/1996 | Crowley | |
| 5,673,704 A | 10/1997 | Marchlinski et al. | |
| 5,730,127 A | 3/1998 | Avitall | |
| 5,759,159 A * | 6/1998 | Masreliez | 600/547 |
| 5,836,990 A | 11/1998 | Li | |
| 6,001,093 A | 12/1999 | Swanson et al. | |
| 6,129,669 A * | 10/2000 | Panescu et al. | 600/424 |
| 6,217,574 B1 | 4/2001 | Webster et al. | |
| 6,391,024 B1 | 5/2002 | Sun et al. | |
| 6,423,057 B1 | 7/2002 | He et al. | |
| 6,490,474 B1 | 12/2002 | Willis et al. | |
| 6,569,160 B1 | 5/2003 | Goldin et al. | |
| 6,755,790 B2 | 6/2004 | Stewart et al. | |
| 6,780,182 B2 | 8/2004 | Bowman et al. | |
| 2001/0034501 A1 | 10/2001 | Tom | |
| 2002/0068931 A1 | 6/2002 | Wong et al. | |
| 2003/0065364 A1 | 4/2003 | Wellman et al. | |
| 2003/0093069 A1 | 5/2003 | Panescu et al. | |
| 2004/0243018 A1 | 12/2004 | Organ et al. | |
| 2005/0054944 A1* | 3/2005 | Nakada et al. | 600/547 |
| 2005/0222554 A1* | 10/2005 | Wallace et al. | 606/1 |

FOREIGN PATENT DOCUMENTS

| | | |
|---|---|---|
| EP | 1586281 | 4/2009 |
| WO | WO-98/46149 | 10/1998 |

* cited by examiner

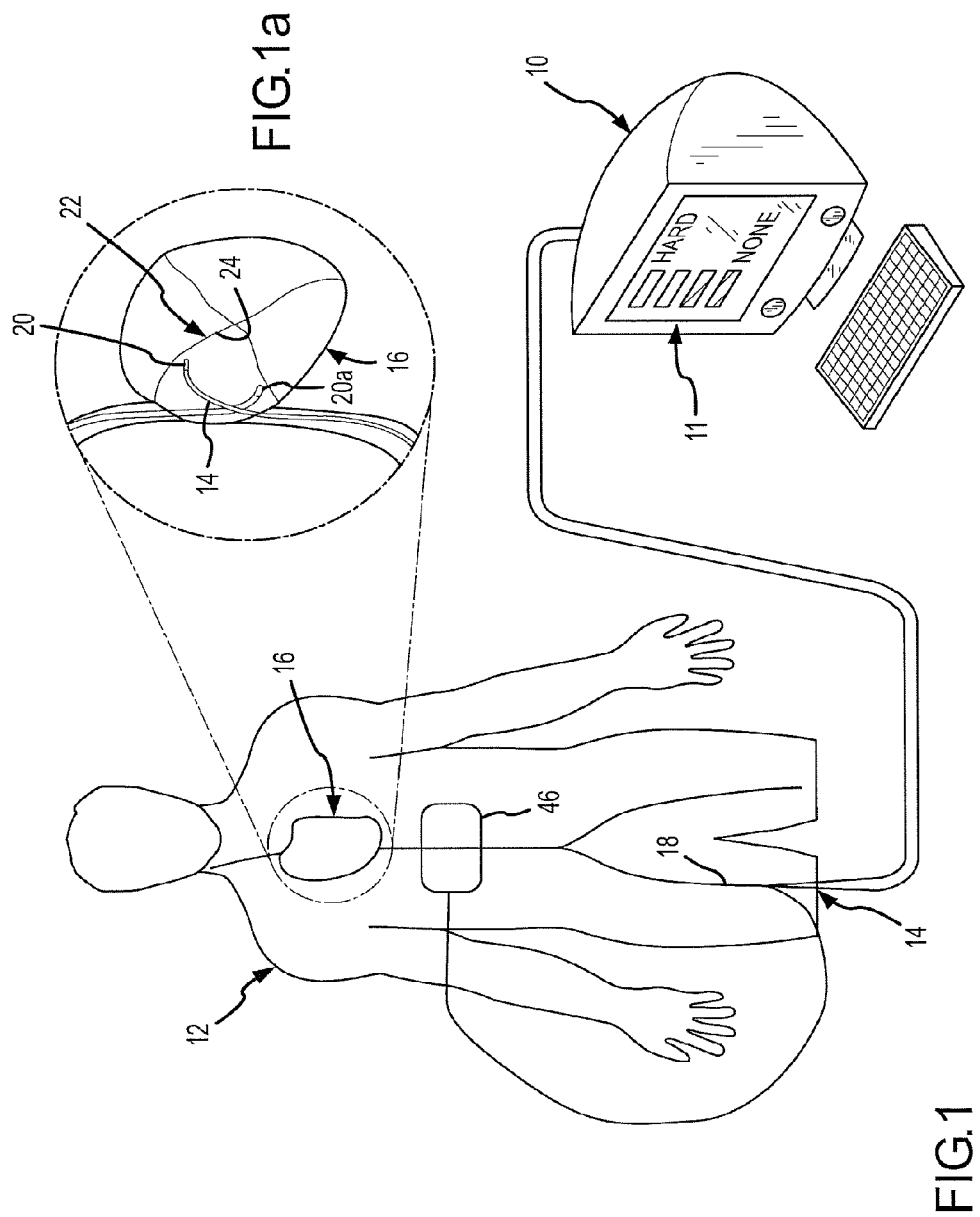

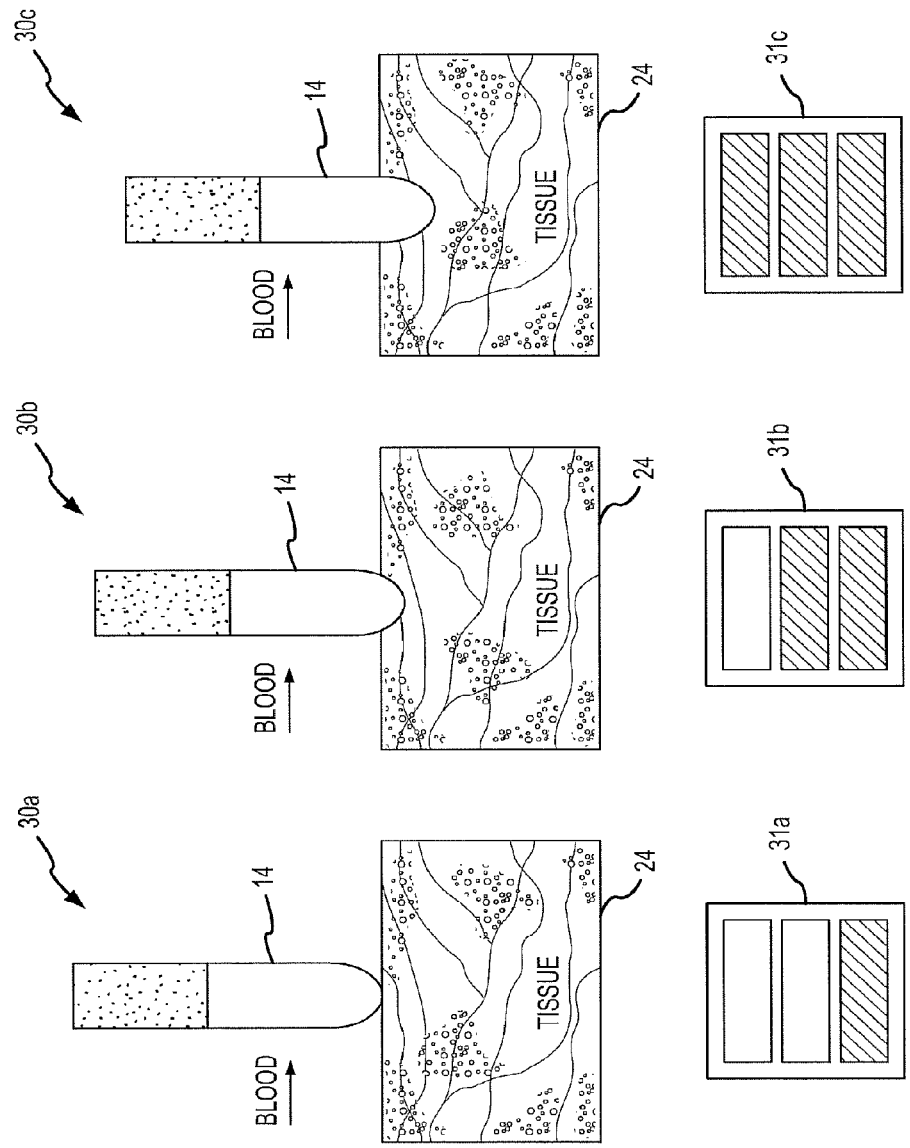

ASSESSMENT OF ELECTRODE COUPLING FOR TISSUE ABLATION

CROSS-REFERENCE TO RELATED APPLICATIONS

This application is a national stage filing based upon international application no. PCT/US2006/061713, filed 6 Dec. 2006 (the '713 application), which claims the benefit of U.S. provisional application No. 60/748,234, filed on 6 Dec. 2005 (the '234 application), as well as U.S. patent application No. 60/829,297, filed 12 Oct. 2006 (the '297 application). The '713 application, the '234 application and the '297 application are incorporated herein by reference. This application is also related to international application no. PCT/US2006/046565, filed 6 Dec. 2006 (the '565 application), international application no. PCT/US2006/061716, filed 6 Dec. 2006 (the '716 application), international application no. PCT/US2006/061712, filed 6 Dec. 2006 (the '712 application), international application no. PCT/US2006/061714, filed 6 Dec. 2006 (the '714 application), international application no. PCT/US2006/061710, filed 6 Dec. 2006 (the '710 application), international application no PCT/US2006/061711 filed 6 Dec. 2006 (the '711 application), and international application no. PCT/US2006/046816, filed 6 Dec. 2006 (the '816 application). The '565 application, the '716 application, the '712 application, the '714 application, the '710 application, the '711 application and the '816 application are incorporated herein by reference.

BACKGROUND OF THE INVENTION a. Field of the Invention

The instant invention is directed toward an electrode catheter and a method for using the electrode catheter for tissue ablation. In particular, the electrode catheter of the present invention may comprise a circuit to assess electrode-tissue contact and electrical coupling for applying ablative energy (e.g., RF energy) to target tissue.

b. Background Art

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, lesions may be formed at specific locations in cardiac tissue via coagulation necrosis to lessen or eliminate undesirable atrial fibrillations.

Several difficulties may be encountered, however, when attempting to form lesions at specific locations using some existing ablation electrodes. One such difficulty encountered with existing ablation electrodes is how to ensure adequate tissue contact and electrical coupling. Electrode-tissue contact is not readily determined using conventional techniques such as fluoroscopy. Instead, the physician determines electrode-tissue contact based on his/her experience using the electrode catheter. Such experience only comes with time, and may be quickly lost if the physician does not use the electrode catheter on a regular basis. In addition, when forming lesions in a heart, the beating of the heart further complicates matters, making it difficult to determine and maintain sufficient contact pressure between the electrode and the tissue for a sufficient length of time to form a desired lesion. If the contact between the electrode and the tissue cannot be properly maintained, a quality lesion is unlikely to be formed. Similarly, information on electrical coupling between the electrode and the target tissue is not readily available a priori to determine how much ablative energy may be absorbed in the tissue during ablation. Instead, the physician uses generalized pre-determined ablation parameters, such as power and duration, based on his/her experience to perform ablation procedures with the electrode catheter. Such experience may lead to deficiencies, inefficiencies and complications, such as inadequate lesion formation, premature high impedance shut-off, tissue charring, and thrombus formation.

BRIEF SUMMARY OF THE INVENTION

It is desirable to be able to assess electrode-tissue contact and electrical coupling for electrode catheters used for tissue ablation procedures. Although radio frequency (RF) ablative energy is predominately resistive heating at typical operating frequencies of about 500 kHz, at lower frequencies there exist capacitances in the patient's blood and tissue. The combined effects of resistance and capacitance at the blood-tissue interface can be measured (e.g., as impedance) to automatically assess different contact conditions between the electrode and a target tissue.

An exemplary electrode catheter system may comprise an electrode adapted to apply electric energy. A measurement circuit adapted to measure impedance may be implemented between the electrode and ground as the electrode approaches a target tissue. A processor or processing units may be implemented to determine a contact condition for the target tissue based at least in part on reactance of the impedance measured by the measurement circuit. In another embodiment, the contact condition may be based on the phase angle of the impedance.

An exemplary electrode catheter system may comprise an electrode adapted to apply electric energy. A measurement circuit adapted to measure impedance may be implemented between the electrode and ground as the electrode approaches a target tissue. A processor or processing units may be implemented to determine an electrical coupling condition for the target tissue based at least in part on reactance of the impedance measured by the measurement circuit. In another embodiment, the electrical coupling condition may be based on the phase angle of the impedance.

An exemplary method of assessing electrode-tissue contact for tissue ablation may comprise: measuring impedance between an electrode and ground as the electrode approaches a target tissue, separating a reactance component from the measured impedance, and indicating a contact condition for the target tissue based at least in part on the reactance component.

An exemplary method of assessing electrode-tissue electrical coupling for tissue ablation may comprise: measuring impedance between an electrode and ground as the electrode approaches a target tissue, separating a reactance component from the measured impedance, and indicating electrical coupling condition for the target tissue based at least in part on the reactance component.

Another exemplary method of assessing electrode-tissue contact for tissue ablation may comprise: directly measuring a phase angle between an electrode and ground as the electrode approaches a target tissue, and indicating a contact condition for the target tissue based at least in part on the phase angle.

Another exemplary method of assessing electrode-tissue electrical coupling for tissue ablation may comprise: directly measuring a phase angle between an electrode and ground as the electrode approaches a target tissue, and indicating electrical coupling condition for the target tissue based at least in part on the phase angle.

The contact condition may be conveyed to the user (e.g., a physician or technician), e.g., at a display device or other interface. The user may then use the contact condition as feedback to properly position the electrode catheter on the target tissue with the desired level of contact for the ablation procedure. For example, the user may increase contact if the contact condition indicates insufficient contact. Or for example, the user may reduce contact if the contact condition indicates too much contact.

The electrical coupling condition may be conveyed to the user (e.g., a physician or technician), e.g., at a display device or other interface. The user may then use the electrical coupling condition as feedback to properly position the electrode catheter on the target tissue with the desired level of coupling for the ablation procedure. For example, the user may increase coupling if the coupling condition indicates insufficient coupling. Or for example, the user may reduce coupling if the coupling condition indicates too much coupling.

It is also noted that in exemplary embodiments, a current source (or alternatively, a voltage source) may be used to administer the electrical energy. This source can be the same source that is used for the ablation procedure and is used to "ping" during positioning of the electrode, or it can be a separately provided source. In any event, a constant current source (or constant voltage source) may be used. Alternatively, a variable current source (or a variable voltage source), such as an ablation source operating in a mode that is adaptive to tissue temperature. Furthermore, a plurality of the current sources (or voltage sources) may be used. The plurality of current sources (or voltage sources) may be operative either in a concurrent, sequential, or temporally overlapping mode.

A number of additional aspects of the present invention exist. What may be characterized as first through seventh aspects of the present invention each may be utilized to assess a coupling between an electrode and tissue, which hereafter may be referred to as an "electrode coupling." This electrode coupling may be in the form of a mechanical coupling between the electrode and tissue, or stated another way a condition or state in which there is physical contact between the electrode and tissue. Another embodiment has this electrode coupling being in the form of an electrical coupling between the electrode and tissue. Electrical coupling may be referred to as a condition or state when a sufficient amount of electrical energy is transferred from the electrode to tissue. It should also be appreciated that there may be one or more "degrees" of electrode coupling, and that one or more benchmarks associated with a particular degree of electrode coupling may be tissue dependent.

A first aspect of the present invention is embodied by a medical system/method for performing a medical procedure on tissue. A first electrode may be disposed in a certain position relative to tissue, and a first electrical signal may be sent to the first electrode. A phase angle associated with the provision of this first electrical signal to the first electrode is used to assess a coupling between the first electrode and the tissue (electrode coupling). More specifically, such a phase angle may be compared with at least one other phase angle value to assess the coupling between the electrode and the tissue.

Various refinements exist of the features noted in relation to the first aspect of the present invention. Further features may also be incorporated in the first aspect of the present invention as well. These refinements and additional features may exist individually or in any combination. Initially, the features discussed below in relation to the fifth aspect may be incorporated into this first aspect.

At least one phase angle benchmark value may be provided for the phase angle comparison in accordance with the first aspect. In one embodiment, this phase angle benchmark value is stored within a data structure or is otherwise accessible by a phase angle comparator or the like. In one embodiment, a phase angle benchmark value is associated with an insufficient coupling condition. In another embodiment, a phase angle benchmark value is associated with an elevated or excessive coupling condition.

In one embodiment of the first aspect, one or more categories or ranges may be provided for a phase angle comparison to assess the electrode coupling. Any appropriate number of phase angle categories or ranges may be used, and these phase angle categories or ranges may be determined or set in any appropriate manner (e.g., empirically). For instance: 1) a first range may include those phase angles that are associated with an insufficient coupling condition, and which may be utilized by a phase angle comparator or the like to determine if a phase angle associated with the first electrical signal is within this first range; 2) a second range may include those phase angles that are associated with a sufficient coupling condition, and which may be utilized by a phase angle comparator or the like to determine if a phase angle associated with the first electrical signal is within this second range; and 3) a third range may include those phase angles that are associated with an elevated or excessive coupling condition, and which may be utilized by a phase angle comparator or the like to determine if a phase angle associated with the first electrical signal is within this third range. Each of these first, second, and third ranges could be used individually to compare with a phase angle value associated with the first electrical signal, or may be used in any appropriate combination with each other. It should be appreciated that what is "insufficient," "sufficient," "elevated/excessive" may be dependent upon the tissue being coupled with the first electrode, as well as one or more other factors.

A phase angle associated with the first electrical signal at a certain point in time of a medical procedure may be determined in any appropriate manner and for purposes of assessing the electrode coupling at this certain point in time in accordance with the first aspect. It of course may be desirable to assess the electrode coupling on some predetermined temporal basis or otherwise in accordance with some predefined function (e.g., assess a phase angle associated with the first electrical signal every "x" seconds during at least part of a medical procedure). In one embodiment, the phase angle that is associated with the first electrical signal is a phase angle between a current being provided to the first electrode and a voltage that exists between the first electrode and another electrode such as a return electrode.

A second aspect of the present invention is embodied by a medical system/method for performing a medical procedure on tissue. A first electrode may be disposed in a certain position relative to tissue, and a first electrical signal may be sent to the first electrode. A reactance associated with the provision of this first electrical signal to the first electrode is used to assess a coupling between the first electrode and the tissue (electrode coupling). More specifically, such a reactance may be compared with at least one other reactance value to assess the coupling between the electrode and the tissue.

Various refinements exist of the features noted in relation to the second aspect of the present invention. Further features may also be incorporated in the second aspect of the present invention as well. These refinements and additional features may exist individually or in any combination. Initially, the features discussed below in relation to the fifth aspect may be incorporated into this second aspect.

At least reactance benchmark value may be provided for the reactance comparison in accordance with the second aspect. In one embodiment, this reactance benchmark value is stored within a data structure or is otherwise accessible by a reactance comparator or the like. In one embodiment, a reactance benchmark value is associated with an insufficient coupling condition. In another embodiment, a reactance benchmark value is associated with an elevated or excessive coupling condition.

In one embodiment of the second aspect, one or more categories or ranges may be provided for a reactance comparison to assess the electrode coupling. Any appropriate number of reactance categories or ranges may be used, and these reactance categories or ranges may be determined or set in any appropriate manner (e.g., empirically). For instance: 1) a first range may include those reactance values that are associated with an insufficient coupling condition, and which may be utilized by a reactance comparator or the like to determine if a reactance associated with the first electrical signal is within this first range; 2) a second range may include those reactance values that are associated with a sufficient coupling condition, and which may be utilized by a reactance comparator or the like to determine if a reactance associated with the first electrical signal is within this second range; and 3) a third range may include those reactance values that are associated with an elevated or excessive coupling condition, and which may be utilized by a reactance comparator or the like to determine if a reactance associated with the first electrical signal is within this third range. Each of these first, second, and third ranges could be used individually to compare with a reactance value associated with the first electrical signal, or used in any appropriate combination with each other. It should be appreciated that what is "insufficient," "sufficient," or "elevated/excessive" may be dependent upon the tissue being coupled with the first electrode, as well as one or more other factors.

A reactance associated with the first electrical signal at a certain point in time of a medical procedure may be determined in any appropriate manner and for purposes of assessing the electrode coupling at this certain point in time in accordance with the second aspect. It of course may be desirable to assess the electrode coupling on some predetermined temporal basis or otherwise in accordance with some predefined function (e.g., assess a reactance associated with the first electrical signal every "x" seconds during at least part of a medical procedure). In one embodiment, the reactance that is associated with the first electrical signal is a reactance associated with the electrical path between the first electrode and another electrode such as a return electrode.

A third aspect of the present invention is embodied by a medical system/method for performing a medical procedure on tissue. A first electrode may be disposed in a certain position relative to tissue, and a first electrical signal may be sent to the first electrode. What may be characterized as an impedance components ratio associated with the provision of this first electrical signal to the first electrode is used to assess a coupling between the first electrode and the tissue (electrode coupling). This "impedance components ratio" is a ratio of two component values that define an impedance (e.g., resistance, reactance, impedance) that is associated with the provision of the first electrical signal. More specifically, such an impedance components ratio may be compared with at least one other impedance components ratio value to assess the coupling between the electrode and the tissue.

A fourth aspect of the present invention is embodied by a medical system/method for performing a medical procedure on tissue. A first electrode may be disposed in a certain position relative to tissue, and a first electrical signal may be sent to the first electrode. The development of an elevated or excessive coupling condition (e.g., mechanical, electrical, or both) may be identified through an appropriate assessment.

Various refinements exist of the features noted in relation to the fourth aspect of the present invention. Further features may also be incorporated in the fourth aspect of the present invention as well. These refinements and additional features may exist individually or in any combination. Initially, the features discussed below in relation to the fifth aspect may be incorporated into this fourth aspect.

One or more parameters may be monitored/assessed for purposes of identifying the existence of an elevated or excessive coupling condition between the first electrode and tissue in the case of the fourth aspect, including without limitation impedance, phase angle (e.g., in accordance with the first aspect), reactance (e.g., in accordance with the second aspect), and target frequency (e.g., in accordance with the seventh aspect discussed below). A reactance (e.g., of a portion of an electrical circuit that extends from the first electrode, through a patient's body, and to a return electrode) may be compared to at least one reactance benchmark value to determine if an excessive coupling condition exists. In one embodiment, an elevated or excessive coupling condition is equated with a reactance that is less than a predetermined negative reactance value. A phase angle (e.g., a phase angle between the current at the first electrode, and the voltage between the first electrode and a return electrode) also may be compared to at least one phase angle benchmark value to determine if an elevated or excessive coupling condition exists. In one embodiment, an elevated or excessive coupling condition is equated with a phase angle that is less than a predetermined negative phase angle value.

That frequency for the first electrical signal at which the phase angle is at a certain, preset value (e.g., a phase angle between the current at the first electrode, and the voltage between the first electrode and a return electrode) may be referred to as a "target frequency", and this target frequency may be compared to at least one frequency benchmark value to determine if an elevated or excessive coupling condition exists for purposes of this fourth aspect. In one embodiment, an elevated or excessive coupling condition is equated with having a target frequency that is greater than a predetermined frequency value. That frequency for the first electrical signal at which an inductance (e.g., of a portion of an electrical circuit that extends from the first electrode, through a patient's body, and to a return electrode) is at a certain, preset value may define a target frequency as well, and this target frequency may be compared to at least one frequency benchmark value to determine if an elevated or excessive coupling condition exists. In one embodiment, an elevated or excessive coupling condition is equated with having a target frequency that is greater than a predetermined frequency value. Generally, an appropriate electrical parameter may be associated with a target frequency, and any appropriate value may be used for this electrical parameter for purposes of the target frequency. Frequencies above a target frequency may be associated with a certain condition, frequencies below a target frequency may be associated with a certain condition, or both.

A fifth aspect of the present invention is embodied by a medical system/method for performing a medical procedure on tissue. A first electrode may be disposed in a certain position relative to tissue, and a first electrical signal that provides a first current may be sent to the first electrode. This first current is used to perform a first medical procedure (e.g., ablation of heart tissue). A coupling between the first electrode and the tissue is also assessed using this first current.

Various refinements exist of the features noted in relation to the fifth aspect of the present invention. Further features may also be incorporated in the fifth aspect of the present invention as well. These refinements and additional features may exist individually or in any combination. The coupling between the first electrode and the tissue in the case of the fifth aspect may be assessed in any appropriate parameter. This assessment may be based upon impedance comparisons, phase angle comparisons (e.g., in accordance with the first aspect), reactance comparisons (e.g., in accordance with the second aspect), and target frequency comparisons (e.g., in accordance with the seventh aspect discussed below).

A second electrical signal that provides a second current may be sent to the first electrode in the case of the fifth aspect. The coupling between the first electrode and the tissue may also be assessed using this second signal. Various characterizations may be made in relation to the second electrical signal, and which apply individually or in any combination: 1) the second current may be less than the first current; 2) the first and second electrical signals may be at least generally of the same frequency; and 3) the first and second signals may be sent sequentially or other than simultaneously, for instance by switching from one electrical power source to another electrical power source. In the latter regard, a switch may be disposed in one position to interconnect the first electrode with a first electrical power source (e.g., an assessment power source), and a first electrode coupling assessment module may be used to assess electrode coupling. Disposing this switch into another position may interconnect the first electrode with a second electrical power source (e.g., an ablation power source), and a second electrode coupling assessment module may be used to assess electrode coupling. These first and second electrode coupling assessment modules may be of a common configuration.

A sixth aspect of the present invention is embodied by a medical system/method for performing a medical procedure on tissue. In one embodiment, a first catheter having a first electrode is positioned within a first chamber of a patient's heart (e.g., the left atrium), along with a second catheter having a second electrode. In another embodiment, first and second electrode tips (e.g., associated with different catheters; associated with a common catheter) are positioned within a first chamber of the heart. In each case, a first electrical signal may be sent to the first electrode for performing a first medical procedure, and a coupling between the first electrode and tissue may be assessed using this first electrical signal.

Various refinements exist of the features noted in relation to the sixth aspect of the present invention. Further features may also be incorporated in the sixth aspect of the present invention as well. These refinements and additional features may exist individually or in any combination. The coupling between the first electrode and the tissue in the case of the sixth aspect may be assessed in any appropriate parameter. This assessment may be based upon impedance comparisons, phase angle comparisons (e.g., in accordance with the first aspect), reactance comparisons (e.g., in accordance with the second aspect), and target frequency comparisons (e.g., in accordance with the seventh aspect discussed below). In addition, the features discussed above in relation to the fifth aspect may be incorporated into this sixth aspect.

A seventh aspect of the present invention is embodied by a medical system/method for performing a medical procedure on tissue. A first electrode may be disposed in a certain position relative to tissue, and a first electrical signal may be sent to the first electrode. One or more frequencies may be analyzed to identify a frequency where an electrical parameter is of certain value (where "value" includes a certain range of values).

Various refinements exist of the features noted in relation to the seventh aspect of the present invention. Further features may also be incorporated in the seventh aspect of the present invention as well. These refinements and additional features may exist individually or in any combination. A target frequency may be where a frequency provides a zero phase angle (e.g., a phase angle between a current being provided to the first electrode and a voltage that exists between the first electrode and another electrode such as a return electrode). A zero frequency also may be where a frequency provides an inductance that is zero (e.g., an inductance of a portion of an electrical circuit that extends from the first electrode, through a patient's body, and to a return electrode). Any electrical parameter may be used for purposes of the target frequency, and this electrical parameter may be of any appropriate value for purposes of a target frequency. In one embodiment, a target frequency is identified by sequentially providing a plurality of electrical signals at different frequencies (e.g., using a frequency sweep), and determining which of these electrical signals generates an electrical parameter of a requisite value. In another embodiment, an electrical signal that includes a plurality of frequencies is sent to the first electrode. Filters may be used to allow each of the various frequencies from this common electrical signal to be separately analyzed to determine if any of these frequencies generates an electrical parameter of a requisite value.

A target frequency may be used to assess the coupling between the first electrode and tissue in the case of the seventh aspect. In this regard, at least one frequency benchmark value may be provided for a frequency comparison in accordance with the seventh aspect to assess electrode coupling. In one embodiment, this frequency benchmark value is stored within a data structure or is otherwise accessible by a frequency comparator or the like. In one embodiment, a frequency benchmark value is associated with an insufficient coupling condition. In another embodiment, a frequency benchmark value is associated with an elevated or excessive coupling condition.

In one embodiment of the seventh aspect, one or more categories or ranges may be provided for a frequency comparison to assess electrode coupling. Any appropriate number of frequency categories or ranges may be used, and these frequency categories or ranges may be determined or set in any appropriate manner (e.g., empirically). For instance: 1) a first range may include those frequencies that are associated with an insufficient coupling condition, and which may be utilized by a frequency comparator or the like to determine if the target frequency is within this first range; 2) a second range may include those frequencies that are associated with a sufficient coupling condition, and which may be utilized by a frequency comparator or the like to determine if the target frequency is within this second range; and 3) a third range may include those frequencies that are associated with an elevated or excessive coupling condition, and which may be utilized by a frequency comparator or the like to determine if the target frequency is within this third range. Each of these first, second, and third ranges could be used individually to compare with a target frequency, or may be used in any appropriate combination with each other. It should be appreciated that what is "insufficient," "sufficient," or "elevated/excessive" may be dependent upon the tissue being coupled with the first electrode, as well as one or more other factors.

There are a number of features or the like that are applicable to each of the first through the seventh aspects, and which will now be summarized. The first electrode may be of any appropriate size, shape, configuration, and/or type, and further may be used to execute any type of medical procedure (e.g., ablation). In one embodiment, the first electrode is in the form of a catheter electrode.

The first electrical signal may be at any appropriate frequency in the case of the first through the seventh aspects. In one embodiment and except in the case of the seventh aspect, only a single frequency is required for purposes of providing an electrode coupling assessment. Any appropriate electrical power source or signal generator may be used to provide the first electrical signal or any other electrical signal. Each such electrical power source or signal generator may be continually interconnected with the first electrode, or may be electrically interconnected as desired/required through operation of a switch or the like.

A return electrode may be used in combination with the first electrode to execute a medical procedure using the first electrode in the case of the first through the seventh aspects, and which also may be used for an electrode coupling assessment. The following features relating to such a return electrode may be used individually or in any appropriate combination: 1) each of the first electrode and the return electrode may be in the form of a catheter electrode, and each such catheter electrode may be independently maneuverable; 2) the return electrode may utilize a larger surface area than the first electrode; and 3) each of the first electrode and return electrode may be disposable in a common chamber of the heart, such as the left atrium.

Any electrode coupling assessment used by the first through the seventh aspects may utilize at least one electrode coupling assessment module (e.g., an electrical circuit). Each such electrode coupling assessment module may be incorporated in any appropriate manner and at any appropriate location. For instance, an electrode coupling assessment module may be incorporated into the catheter, may be in the form of a standalone unit, may be incorporated by an electrical power generator, may be incorporated by an electrophysiology mapping system, or may be incorporated by electrophysiology signal recording system.

Each of the first through the seventh aspects may be used to identify the existence of an elevated or excessive coupling condition. The ability to identify the existence of such an elevated or excessive coupling condition may be desirable for a number of reasons. For instance, it may be desirable to avoid an elevated or excessive coupling condition (e.g., to reduce the potential of puncturing a tissue wall or membrane). It also may be desirable to reach an elevated or excessive coupling condition (e.g., to increase the potential of passing the first electrode through a tissue wall or membrane).

Any phase angle comparison used by the first through the seventh aspects may utilize a phase shift circuit to facilitate the measurement/determination of a phase angle. For instance, the phase of a current signal being provided to the first electrode may be shifted an appropriate amount (e.g., by 90°). It also may be desirable to compensate for a residual phase shift for purposes of any electrode coupling assessment based upon a phase angle comparison. That is, a phase shift may be indicated to exist for an electrode coupling assessment, when there in fact should be no phase difference under the current circumstances.

The result of any electrode coupling assessment used by the first through seventh aspects may be output in any appropriate manner to one or more locations. This output may be in the form of one or more of visual feedback, audible feedback, or physical feedback. For instance, a bar graph or other display may be utilized to visually convey the current degree of the electrode coupling. It may be desirable to scale/amplify the output of the electrode coupling assessment.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1 is a diagrammatic illustration of an exemplary tissue ablation system which may be implemented to assess electrode-tissue contact during a tissue ablation procedure for a patient.

FIG. 1a is a detailed illustration of the patient's heart in FIG. 1, showing the electrode catheter after it has been moved into the patient's heart.

FIG. 2b illustrates exemplary levels of mechanical contact or coupling between the electrode catheter and a target tissue.

DETAILED DESCRIPTION OF THE INVENTION

Figure 2A:
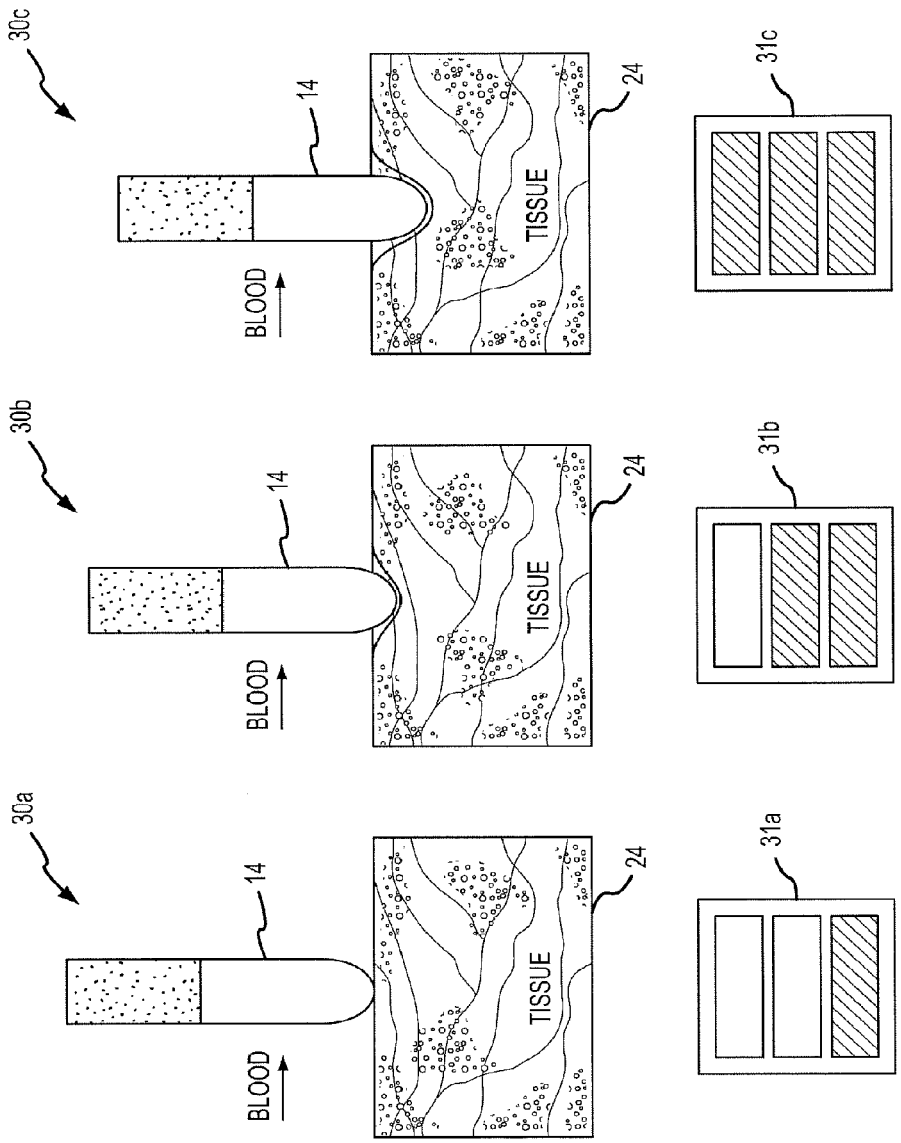
FIG. 2a illustrates exemplary levels of electrical contact or coupling between the electrode catheter and a target tissue.

Exemplary embodiments of a tissue ablation system and methods of use to assess electrode-tissue contact and electrical coupling are depicted in the figures. As described further below, the tissue ablation system of the present invention provides a number of advantages, including, for example, the ability to apply a reasonable amount of ablative energy to a target tissue while mitigating electrode-tissue contact and coupling problems. The invention also facilitates enhanced tissue contact and electrical coupling in difficult environments (e.g., during lesion formation on a surface inside a beating heart).

FIG. 1 is a diagrammatic illustration of an exemplary electrode catheter system 10 which may be implemented to assess electrode-tissue contact during a tissue ablation procedure for a patient 12. Catheter system 10 may include an electrode catheter 14, which may be inserted into the patient 12, e.g., for forming ablative lesions inside the patient's heart 16. During an exemplary ablation procedure, a user (e.g., the patient's physician or a technician) may insert the electrode catheter 14 into one of the patient's blood vessels 18, e.g., through the leg (as shown in FIG. 1) or the patient's neck. The user, guided by a real-time fluoroscopy imaging device (not shown), moves the electrode catheter 14 into the patient's heart 16 (as shown in more detail in FIG. 1a).

When the electrode catheter 14 reaches the patient's heart 16, electrodes 20 at the tip of the electrode catheter 14 may be implemented to electrically map the myocardium 22 (i.e., muscular tissue in the heart wall) and locate a target tissue 24. After locating the target tissue 24, the user must move the electrode catheter 14 into contact and electrically couple the catheter electrode 14 with the target tissue 24 before applying ablative energy to form an ablative lesion or lesions. The electrode-tissue contact refers to the condition when the catheter electrode 14 physically touches the target tissue 24 thereby causing a mechanical coupling between the catheter electrode 14 and the target tissue 24. Electrical coupling refers to the condition when a sufficient portion of electrical energy passes from the catheter electrode 14 to the target tissue 24 so as to allow efficient lesion creation during ablation. For target tissues with similar electrical and mechanical properties, electrical coupling includes mechanical contact. That is, mechanical contact is a subset of electrical coupling. Thus, the catheter electrode may be substantially electrically coupled with the target tissue without being in mechanical contact, but not vice-versa. In other words, if the catheter electrode is in mechanical contact, it is also electrically coupled. The range or sensitivity of electrical coupling, however, changes for tissues with different electrical properties. For example, the range of electrical coupling for electrically conductive myocardial tissue is different from the vessel walls. Likewise, the range or sensitivity of electrical coupling also changes for tissues with different mechanical properties, such as tissue compliance. For example, the range of electrical coupling for the relatively more compliant smooth atrial wall is different from the relatively less compliant pectinated myocardial tissue. The level of contact and electrical coupling are often critical to form sufficiently deep ablative lesions on the target tissue 24 without damaging surrounding tissue in the heart 16. The catheter system 10 may be implemented to measure impedance at the electrode-tissue interface and assess the level of contact (illustrated by display 11) between the electrode catheter 14 and the target tissue 24, as described in more detail below.

FIG. 2a illustrates exemplary levels of electrical contact or coupling between an electrode catheter 14 and a target tissue 24. FIG. 2b illustrates exemplary levels of mechanical contact or coupling between an electrode catheter 14 and a target tissue 24. Exemplary levels of contact or coupling may include "little or no contact" as illustrated by contact condition 30a, "light to medium contact" as illustrated by contact condition 30b, and "hard contact" as illustrated by contact condition 30c. In an exemplary embodiment, the catheter system 10 may be implemented to display or otherwise output the contact condition for the user, e.g., as illustrated by light arrays 31a-c corresponding to contact conditions 30a-c, respectively.

Contact condition 30a ("little or no contact") may be experienced before the electrode catheter 14 comes into contact with the target tissue 24. Insufficient contact may inhibit or even prevent adequate lesions from being formed when the electrode catheter 14 is operated to apply ablative energy. However, contact condition 30c ("hard contact") may result in the formation of lesions which are too deep (e.g., causing perforations in the myocardium 22) and/or the destruction of tissue surrounding the target tissue 24. Accordingly, the user may desire contact condition 30b ("light to medium contact").

It is noted that the exemplary contact or coupling conditions 30a-c in FIG. 2a-b are shown for purposes of illustration and are not intended to be limiting. Other contact or coupling conditions (e.g., finer granularity between contact conditions) may also exist and/or be desired by the user. The definition of such contact conditions may depend at least to some extent on operating conditions, such as, the type of target tissue, desired depth of the ablation lesion, and operating frequency of the RF radiation, to name only a few examples.

Figure 3:
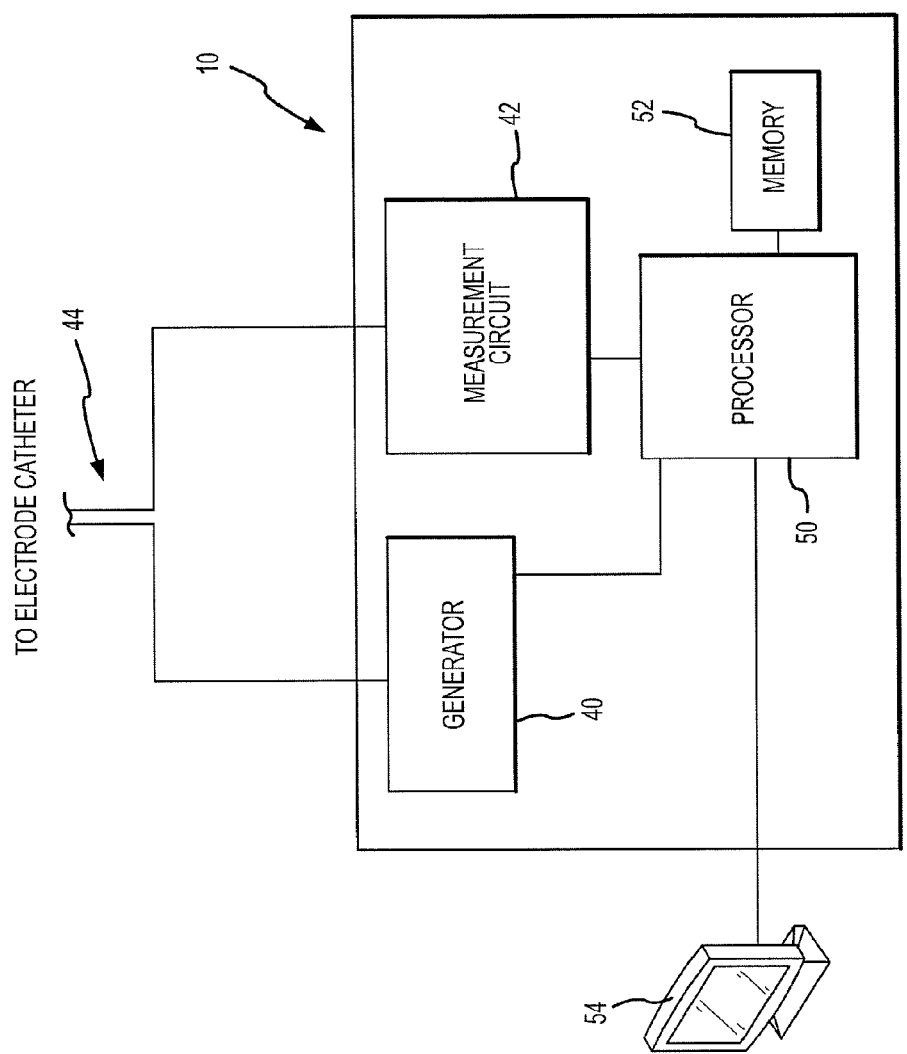
FIG. 3 is a high-level functional block diagram showing the exemplary tissue ablation system of FIG. 1 in more detail.

FIG. 3 is a high-level functional block diagram showing the catheter system 10 in more detail as it may be implemented to assess contact or coupling conditions for the electrode catheter 14. It is noted that some of the components typical of conventional tissue ablation systems are shown in simplified form and/or not shown at all in FIG. 1 for purposes of brevity. Such components may nevertheless also be provided as part of, or for use with the catheter system 10. For example, electrode catheter 14 may include a handle portion, a fluoroscopy imaging device, and/or various other controls, to name only a few examples. Such components are well understood in the medical devices arts and therefore further discussion herein is not necessary for a complete understanding of the invention.

Exemplary catheter system 10 may include a generator 40, such as, e.g., a radio frequency (RF) generator, and a measurement circuit 42 electrically connected to the electrode catheter 14 (as illustrated by wires 44 to the electrode catheter). The electrode catheter 14 may also be electrically grounded, e.g., through grounding patch 46 affixed to the patient's arm or chest (as shown in FIG. 1).

Generator 40 may be operated to emit electrical energy (e.g., RF current) near the tip of the electrode catheter 14. It is noted that although the invention is described herein with reference to RF current, other types of electrical energy may also be used for assessing contact conditions.

In an exemplary embodiment, generator 40 emits a so-called "pinging" (e.g., low) frequency as the electrode catheter 14 approaches the target tissue 24. The "pinging" frequency may be emitted by the same electrode catheter that is used to apply ablative energy for lesion formation. Alternatively, a separate electrode catheter may be used for applying the "pinging" frequency. In such an embodiment, the separate electrode may be in close contact with (or affixed to) the electrode for applying ablative energy so that a contact or coupling condition can be determined for the electrode which will be applying the ablative energy.

The resulting impedance at the electrode-tissue interface may be measured during contact or coupling assessment (or "pinging") using a measurement circuit 42. In an exemplary embodiment, the measurement circuit 42 may be a conventionally available resistance-capacitance-inductance (RCL) meter. Another exemplary measurement circuit which may be implemented for determining the phase angle component is also described in more detail below with reference to FIG. 5. Still other measurement circuits 42 may be implemented and the invention is not limited to use with any particular type or configuration of measurement circuit.

The reactance and/or phase angle component of the impedance measurements may be used to determine a contact or coupling condition. The contact or coupling condition may then be conveyed to the user in real-time for achieving the desired level of contact or coupling for the ablation procedure. For example, the contact or coupling condition may be displayed for the user on a light array (e.g., as illustrated in FIG. 2a-b).

After the user has successfully guided the electrode catheter 14 into the desired contact or coupling condition with the target tissue 24, a generator, such as generator 40 or a second generator, may be operated to generate ablative (e.g., high frequency) energy for forming an ablative lesion or lesions on the target tissue 24. In an exemplary embodiment, the same generator 40 may be used to generate electrical energy at various frequencies both for the impedance measurements (e.g., "pinging" frequencies) and for forming the ablative lesion. In alternative embodiments, however, separate generators or generating units may also be implemented without departing from the scope of the invention.

In an exemplary embodiment, measurement circuit 42 may be operatively associated with a processor 50 and memory 52 to analyze the measured impedance. By way of example, processor 50 may determine a reactance and/or phase angle component of the impedance measurement, and based on the reactance component and/or phase angle, the processor 50 may determine a corresponding contact or coupling condition for the electrode catheter 14. In an exemplary embodiment, contact or coupling conditions corresponding to various reactance and/or phase angles may be predetermined, e.g., during testing for any of a wide range of tissue types and at various frequencies. The contact or coupling conditions may be stored in memory 52, e.g., as tables or other suitable data structures. The processor 50 may then access the tables in memory 42 and determine a contact or coupling condition corresponding to impedance measurement based on the reactance component and/or phase angle. The contact or coupling condition may be output for the user, e.g., at display device 54.

It is noted, that the catheter system 10 is not limited to use with processor 50 and memory 52. In other embodiments, analog circuitry may be implemented for assessing contact conditions based on the impedance measurement and for outputting a corresponding contact condition. Such circuitry may be readily provided by one having ordinary skill in the electronics arts after having become familiar with the teachings herein, and therefore further discussion is not needed.

It is also noted that display device 54 is not limited to any particular type of device. For example, display device 54 may be a computer monitor such as a liquid-crystal display (LCD). Alternatively, display device may be implemented as a light array, wherein one or more light emitting diodes (LED) are activated in the light array to indicate a contact condition (e.g., more lights indicating more contact). Indeed, any suitable output device may be implemented for indicating contact conditions to a user, and is not limited to a display device. For example, the contact condition may be output to the user as an audio signal or tactile feedback (e.g., vibrations) on the handle of the electrode catheter.

It is further noted that the components of catheter system 10 do not need to be provided in the same housing. By way of example, measurement circuit 42 and/or processor 50 and memory 52 may be provided in a handle portion of the electrode catheter 14. In another example, at least part of the measurement circuit 42 may be provided elsewhere in the electrode catheter 14 (e.g., in the tip portion). In still other examples, processor 50, memory 52, and display device 54 may be provided as a separate computing device, such as a personal desktop or laptop computer which may be operatively associated with other components of the catheter system 10.

Figure 4:
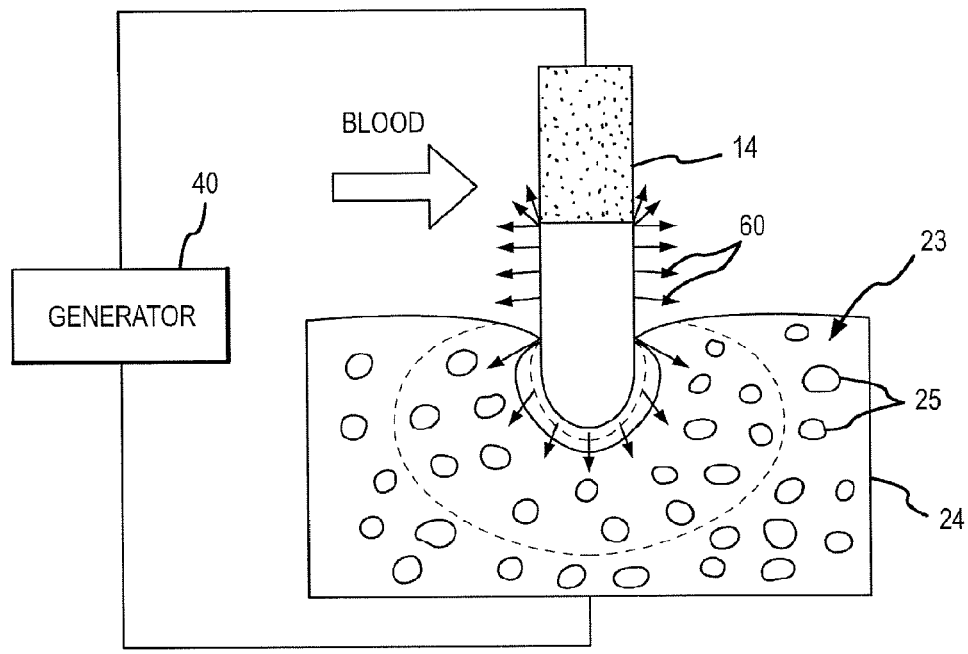
FIG. 4 is a model of the electrode catheter in contact with (or coupled to) target tissue.
Figure 4A:
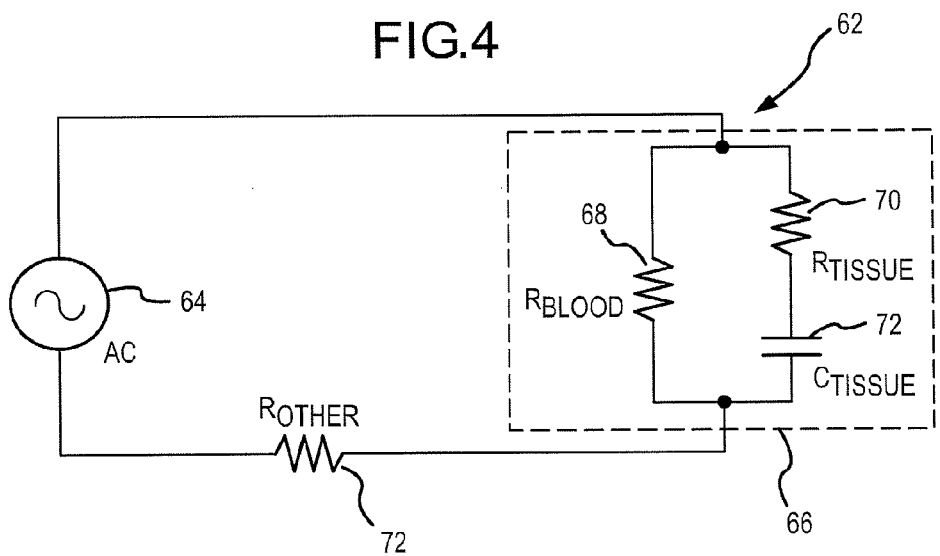
FIG. 4a is a simplified electrical circuit for the model shown in FIG. 4.

Assessing a contact or coupling condition between the electrode catheter 14 and target tissue 24 based on impedance measurements at the electrode-tissue interface may be better understood with reference to FIGS. 4 and 4a. FIG. 4 is a model of the electrode catheter 14 in contact with (or coupled to) target tissue 24. The electrode catheter 14 is electrically connected to the generator 40 (e.g., an RF generator). In an exemplary embodiment, the circuit may be completed through the target tissue 24, showing that current flows through the blood, myocardium, and other organs to the reference electrode, such as a grounding patch 46 on the patient's body (FIG. 1).

As described above, the generator 40 may be operated to generate electrical energy for emission by the electrode catheter 14. Emissions are illustrated in FIG. 4 by arrows 60. Also as described above, generator 40 may emit a "pinging" frequency as the electrode catheter 14 approaches the target tissue 24 for assessing electrode-tissue contact or coupling. In an exemplary embodiment, this "pinging" frequency may be selected such that inductive, capacitive, and resistive effects other than those at the blood-tissue interface do not appreciably affect the impedance measurements.

In an exemplary application, capacitive effects of the blood and at the electrode-blood interface (e.g., between the metal electrode catheter and the blood) were found be minimal or even non-existent at frequencies higher than about 50 kHz. Stray inductance (e.g., due to the relatively thin catheter wires), capacitance and resistance at the electrode interface, and capacitance effects of other organs (e.g., the lungs) were also found to be minimal or even non-existent at frequencies higher than about 50 kHz.

In addition, it was found that resistive effects dominate at the blood-tissue interface for frequencies below 50 kHz because the current flows into the target tissue 24 primarily via the interstitial fluid spaces 23, and the cell membranes 25 (e.g., bi-lipids or "fat") act as an insulator. However, at frequencies greater than about 50 kHz, the cell membranes 25 become conductive, and electrical current penetrates the target tissue 24 through both the interstitial fluid spaces 23 and the cell membranes 25. Accordingly, the cell membranes act as "capacitors" and the resistive effects are reduced at frequencies above about 50 kHz.

To avoid a risk of creating an ablation lesion during contact or coupling assessment, it can be desirable to use a low amount of current and power. A presently preferred range for a current of less than 1 mA is a working frequency in the 50-500 kHz range.

The frequency choice is mostly based on physiological aspect and engineering aspect and is within the purview of one of ordinary skill in the art. For physiological aspect, lower frequencies can introduce measurement errors due to electrode-electrolyte interface. When frequency goes higher to MHz range or above, the parasitic capacitance can become significant. It is noted, however, that the invention is not limited to use at any particular frequency or range of frequencies. The frequency may depend at least to some extent on operational considerations, such as, e.g., the application, the type of target tissue, and the type of electrical energy being used, to name only a few examples.

Assuming, that a desired frequency has been selected for the particular application, the model shown in FIG. 4 may be further expressed as a simplified electrical circuit 62, as shown in FIG. 4*a*. In the circuit 62, generator 40 is represented as an AC source 64. As discussed above, capacitance and resistance at the blood-tissue interface dominate impedance measurements at low frequency operation such as may be used for assessing electrode-tissue contact. Accordingly, other capacitive, inductive, and resistive effects may be ignored and the capacitive-resistive effects at the blood-tissue interface may be represented in circuit 62 by a resistor-capacitor (R-C) circuit 66.

The R-C circuit 66 may include a resistor 68 representing the resistive effects of blood on impedance, in parallel with a resistor 70 and capacitor 72 representing the resistive and capacitive effects of the target tissue 24 on impedance. When the electrode catheter 14 has no or little contact with the target tissue 24, resistive effects of the blood affect the R-C circuit 66, and hence also affect the impedance measurements. As the electrode catheter 14 is moved into contact with the target tissue 24, however, the resistive and capacitive effects of the target tissue 24 affect the R-C circuit 66, and hence also affect the impedance measurements.

The effects of resistance and capacitance on impedance measurements may be better understood with reference to a definition of impedance. Impedance (Z) may be expressed as:

$$Z = R + jX$$

where:
R is resistance from the blood and/or tissue;
j an imaginary number indicating the term has a phase angle of +90 degrees; and
X is reactance from both capacitance and inductance.

It is observed from the above equation that the magnitude of the reactance component responds to both resistive and capacitive effects of the circuit 62. This variation corresponds directly to the level of contact or coupling at the electrode-tissue interface, and therefore may be used to assess the electrode-tissue contact or coupling. By way of example, when the electrode catheter 14 is operated at a frequency of 100 kHz and is primarily in contact with the blood, the impedance is purely resistive and the reactance (X) is close to 0 Ohms When the electrode catheter 14 contacts the target tissue, the reactance component becomes negative. As the level of contact or coupling is increased, the reactance component becomes more negative.

Alternatively, contact or coupling conditions may be determined based on the phase angle. Indeed, determining contact or coupling conditions based on the phase angle may be preferred in some applications because the phase angle is represented as a trigonometric ratio between reactance and resistance. Although the magnitude of the reactance component may be different under varying conditions (e.g., for different patients), the phase angle is a relative measurement which tends to be insensitive to external conditions.

In an exemplary embodiment, the phase angle may be determined from the impedance measurements (e.g., by the processor 50 in FIG. 3). That is, impedance may be expressed as:

$$Z = |Z| \angle \phi$$

where:
|Z| is the magnitude of the impedance; and
φ is the phase angle.
The terms |Z| and φ may further be expressed as:

$$|Z| = \sqrt{R^2 + X^2}; \text{ and } \tan\phi = \frac{X}{R}$$

The phase angle also corresponds directly to the level of contact or coupling at the electrode-tissue interface, and therefore may be used to assess the electrode-tissue contact or coupling. By way of example, when the electrode catheter 14 is operated at a frequency of 100 kHz and is primarily in contact with the blood, the phase angle is close to zero (0). When the electrode catheter 14 contacts the target tissue, the phase angle becomes negative, and the phase angle becomes more negative as the level of contact or coupling is increased. An example is shown in Table 1 for purposes of illustration.

TABLE 1

Phase Angle Relation to Contact Conditions

| Phase Angle | Contact Condition |
|---|---|
| φ > −3° | little or no contact or coupling |
| −3° < φ < −7° | medium contact or coupling |
| −7° < φ < −10° | high contact or coupling |
| φ < −10° | excessive contact or coupling |

Figure 5:
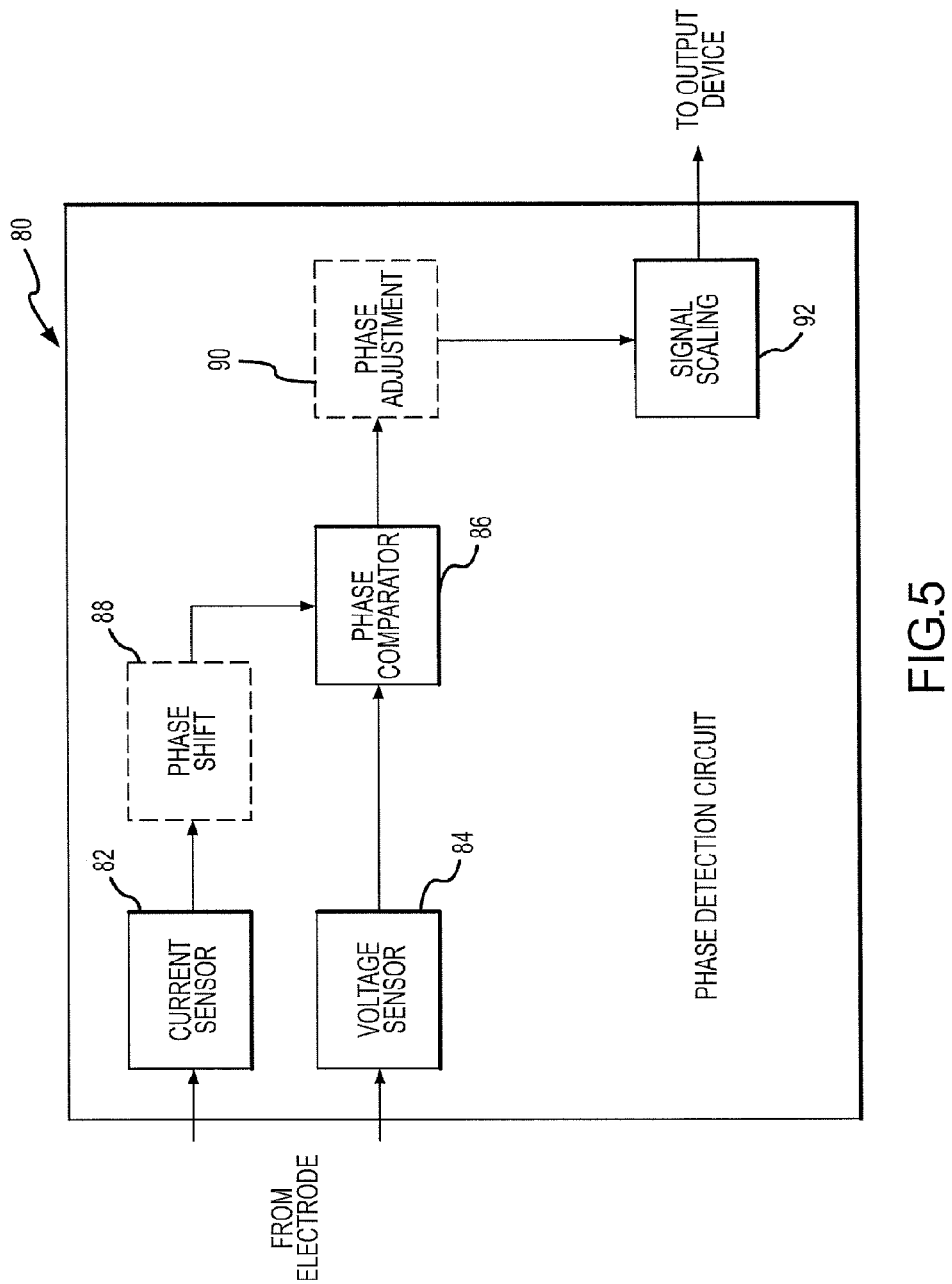
FIG. 5 is an exemplary phase detection circuit which may be implemented in the tissue ablation system for assessing electrode-tissue contact or coupling.

Although impedance measurements may be used to determine the phase angle, in an alternative embodiment, the measurement circuit 42 may be implemented as a phase detection circuit to directly determine the phase angle. An exemplary phase detection circuit 80 is shown in FIG. 5. Phase detection circuit 80 is shown and described with reference to functional components. It is noted that a particular hardware configuration is not necessary for a full understanding of the invention. Implementation of the phase detection circuit 80 in digital and/or analog hardware and/or software will be readily apparent to those having ordinary skill in the electronics art after becoming familiar with the teachings herein.

Exemplary phase detection circuit 80 may include a current sensor 82 and voltage sensor 84 for measuring current and voltage at the electrode-tissue interface. The current and voltage measurements may be input to a phase comparator 86. Phase comparator 86 provides a direct current (DC) output voltage proportional to the difference in phase between the voltage and current measurements.

In one embodiment, the current sensor 82 may be used to measure the ablation current. The sensor can be in series with ablation wire. For example, a Coilcraft CST1 current sensing transformer may be placed in series with the ablation wire. Alternatively, the current wire can pass through holes of a current sensor, with or without physical connection. In addition, the voltage between the ablation electrode and the ground patch can be sensed. This voltage can be attenuated so that it can be fed into a phase sensing circuit. The phase sensing circuit then measures the current and voltage and determines the phase angle between them, which is then correlated to a coupling level. In this way the ablation current can be used to measure the phase angle rather than injecting an additional current for the coupling sensing purpose.

Optionally, current measurements may be phase shifted by phase shift circuit 88 to facilitate operation of the phase comparator 86 by "correcting" phase lag between the measured current and the measured voltage. Also optionally, output from the phase comparator 86 may be "corrected" by phase adjustment circuit 90 to compensate for external factors, such as the type of grounding patch 46 being used. A signal scaling circuit 92 may also be provided to amplify the output (e.g., from milli-volts to volts) for use by various devices (e.g., the processor 50 and display device 54 in FIG. 3).

During ablation, the measured impedance, and its component's resistance and reactance, change with tissue temperature. In such conditions, the change due to changes in tissue temperature provides a measure of lesion formation during ablation.

It is noted that phase detection circuit 80 shown in FIG. 5 is provided as one example, and is not intended to be limiting. Other implementations may also be readily provided by those having ordinary skill in the electronics arts after becoming familiar with the teachings herein without departing from the scope of the invention.

Figure 6:
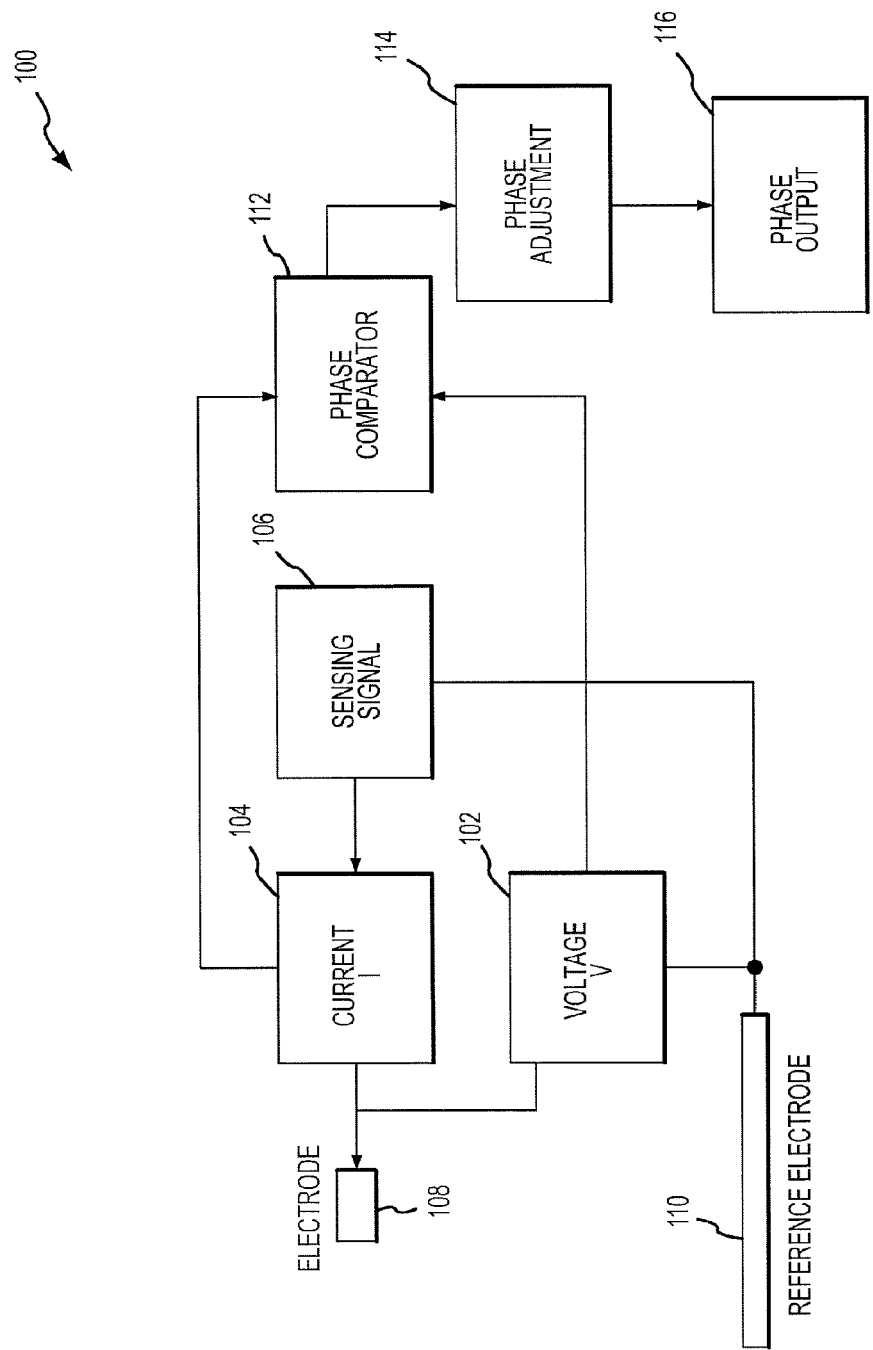
FIG. 6 is an exemplary block diagram showing phase angle measurement for contact sensing and tissue sensing.
Figure 7:
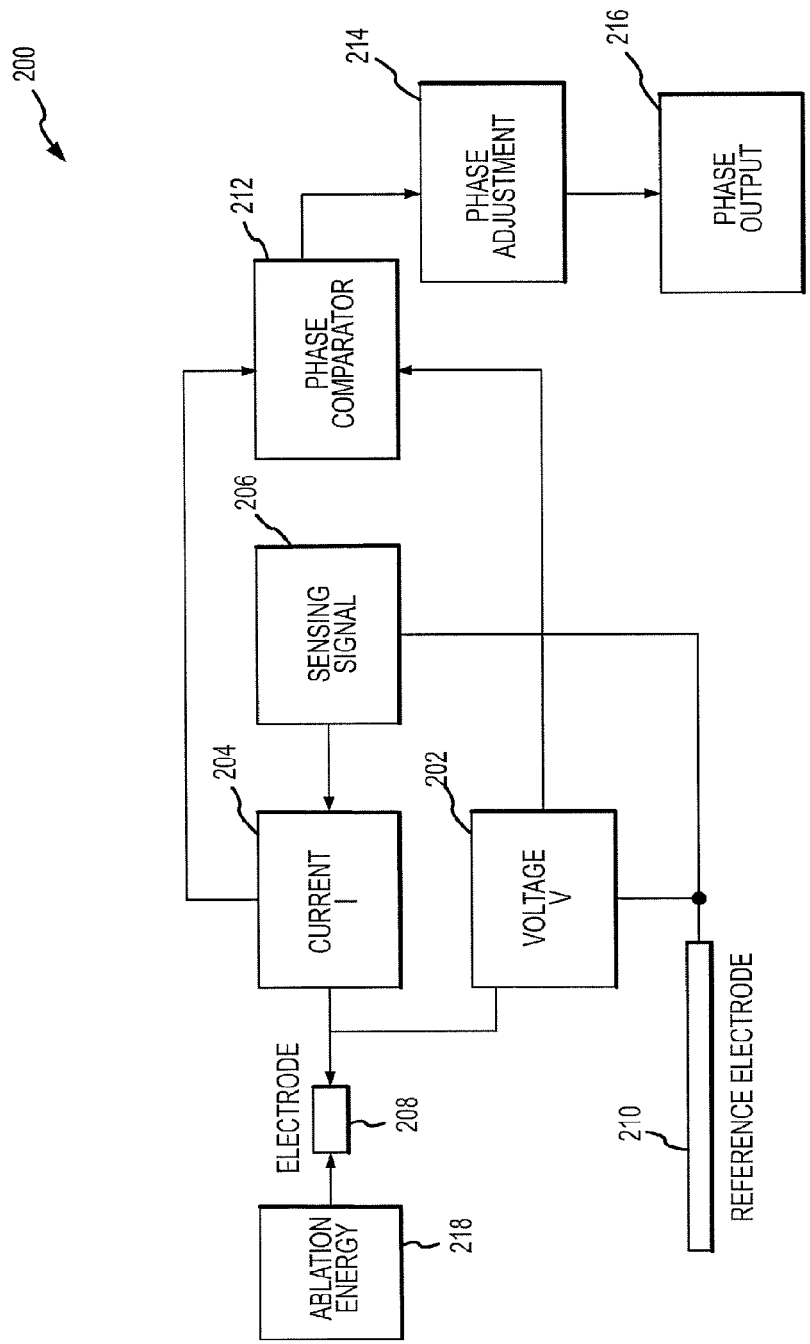
FIG. 7 is an exemplary block diagram showing phase angle measurement during ablation with both ablation energy and a contact sensing signal applied to the ablation electrode at the same time.
Figure 8:
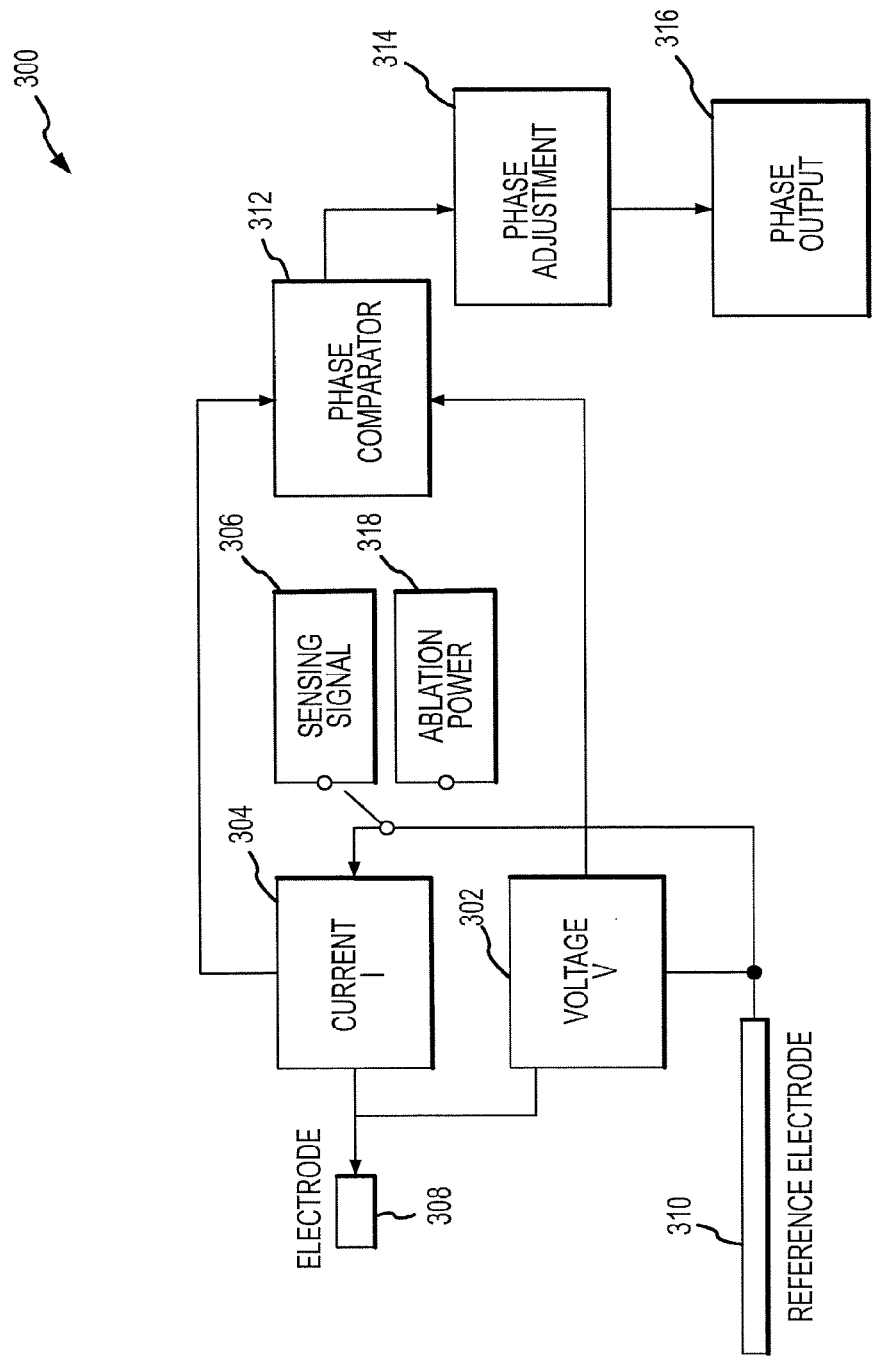
FIG. 8 is an exemplary block diagram showing phase angle measurement during ablation with switching between a sensing signal and ablation power.

Having described exemplary systems for electrode contact assessment, exemplary operational modes may now be better understood with reference to the block diagrams shown in FIGS. 6-8. FIG. 6 is an exemplary block diagram 100 showing phase angle measurement for sensing contact or coupling. FIG. 7 is an exemplary block 200 diagram showing phase angle measurement during ablation with both ablation energy and a contact sensing signal applied to the ablation electrode at the same time. FIG. 8 is an exemplary block diagram 300 showing phase angle measurement during ablation with switching between sensing signal and ablation power. It is noted that 200-series and 300-series reference numbers are used in FIG. 7 and FIG. 8, respectively, to denote similar elements and these elements may not be described again with reference to FIG. 7 and FIG. 8.

As noted above, the phase angle method of sensing contact or coupling is based on the fact that (1) tissue is both more resistive and capacitive than blood, and (2) measured electrode impedance is mostly dependant on the immediate surrounding materials. Thus, when an electrode moves from blood to myocardium, the measured impedance value increases and phase angles change from 0° to negative values (capacitive). Phase angle may be used to represent the contact or coupling levels because phase angle is a relative term of both resistance and reactance. That is, it provides a 0° base line when the electrode is in contact with blood, and becomes increasingly more negative as more contact or coupling is established. It also minimizes the influence of the catheter, instrumentation, and physiological variables.

The phase angle measurement may be made by sampling both electrical voltage (V) 102 and current (I) 104 of a load and calculating the lag between those signals as the phase angle. As shown in FIG. 6, a sensing signal 106 is applied between the ablation electrode 108 and a reference electrode 110. This sensing signal 106 can, for example, be between 50 to 500 kHz at a small amplitude (<1 mA).

Exemplary instruments may be operated as frequencies of, for example but not limited to, 100 kHz, 400 kHz and 485 kHz, depending on the reference electrode configuration. Both current 104 and voltage 102 are sensed. These two signals are transmitted to a phase comparator 112 to calculate phase angle, which corresponds to the contact or coupling condition of the electrode 108. The raw phase angle signal is adjusted in block 114 to compensate for external influence on the phase angle, e.g., caused by the catheter, instrumentation, and physiological variables. It is also conditioned for easy interpretation and interface and then output in block 116 to other equipments for display or further processing.

The phase compensation may be achieved at the beginning of an ablation procedure. First, the catheter electrode is maneuvered to the middle of the heart chamber (e.g., the right atrium or left atrium) so that the electrode 108 only contacts blood. The system measures the phase angle and uses this value as a baseline for zero contact level. This adjustment compensates the fixed phase angles caused by catheter and patient such as catheter wiring, location of the reference electrode and skin or adiposity if external patch is used.

After the initial zero adjustment, the user may maneuver the catheter electrode to one or more desired sites to ablate arrhythmic myocardium. In an exemplary embodiment, the phase angle starts to change when the electrode 108 approaches to say within 3 mm from the myocardium and becomes increasingly more negative as more contact or coupling is established. The user may judge the quality of electrode contact or coupling before administering the ablation energy based on phase angle output. In an exemplary embodiment, this phase angle value is about −3° when a 4 mm ablation electrode actually contacts the myocardium. It is noted that there are at least two methods to measure phase angle during ablation, as described in more detail now with reference to FIG. 7 and FIG. 8.

In FIG. 7, ablation power 218 is applied to the electrode 208 while the sensing signal 206 is applied as well. The ablation and contact sensing operate at different frequencies. Accordingly, with filtering, the phase angle can be measured during ablation without disturbing the ablation of the myocardium.

Another option is to switch the phase measurement between the sensing signal 306 and ablation power 318, as indicated by switch 320 in FIG. 8. When the ablation power 318 is switched off during approach, the small amplitude sensing signal 306 is switched on and used to measure phase angle for sensing contact or coupling. When the ablation power 318 is switched on for the ablation procedure, the voltage and current of the large amplitude ablation power 318 are sensed and used as the contact or coupling indicator during ablation.

Figure 9A:
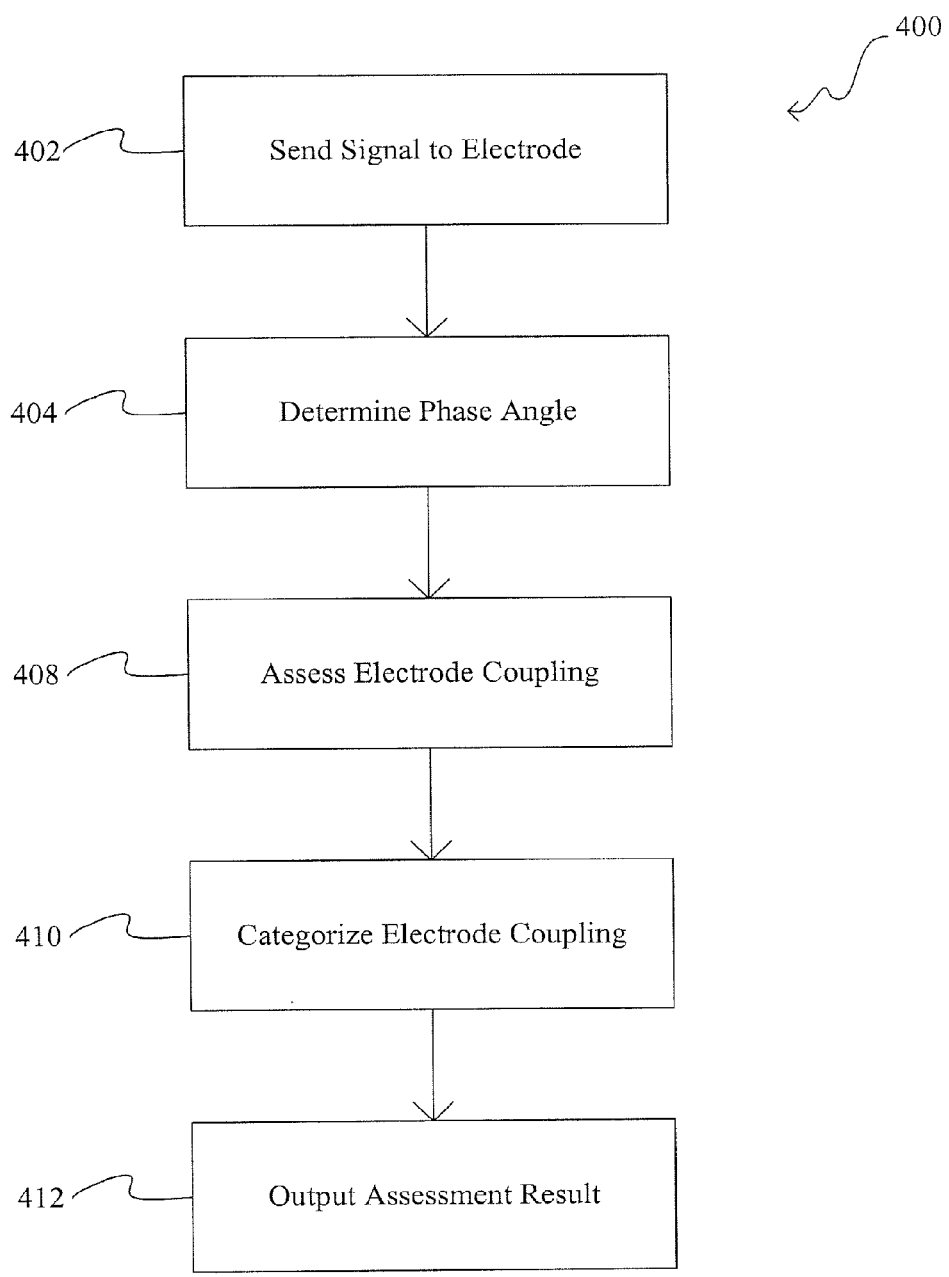
FIG. 9a illustrates one embodiment of a protocol that may be used to assess a coupling between an electrode and tissue based upon a phase angle comparison.

FIG. 9a illustrates one embodiment of an electrode coupling assessment protocol 400 (hereafter "assessment protocol 400") that may be used to assess the coupling of an electrode (e.g., a catheter electrode) with any appropriate tissue, where this assessment is phase angle based. Therefore, the protocol 400 may be used in relation to the embodiments discussed above in relation to FIGS. 6-8. In any case, "coupling" may include an electrical coupling of an electrode with a target tissue, a mechanical coupling between an electrode and the target tissue, or both.

Step 402 of the assessment protocol 400 of FIG. 9a is directed to sending an electrical signal to an electrode. Typically this will be after the electrode has been positioned at least in the general vicinity of the target tissue (e.g., within a heart chamber, such as the left atrium). A phase angle is thereafter determined at step 404, and the electrode coupling is thereafter assessed at step 408 based upon this phase angle. The electrode coupling assessment from step 408 may be categorized through execution of step 410. However, the categorization of step 410 may not be required in all instances. In any case, the result of the assessment from step 408 is output pursuant to step 412.

The electrical signal that is sent pursuant to step 402 of the protocol 400 may be at any appropriate frequency. However, only a single frequency is required to make the assessment for purposes of the protocol 400. The phase angle associated with step 404 may be the phase angle of the impedance. This phase angle may be determined in any appropriate manner, for instance using a phase sensing circuit of any appropriate configuration. In one embodiment and using the electrical signal associated with step 402, the phase angle is determined by measuring the current at the electrode, measuring the voltage between the electrode and another electrode (e.g., a return electrode), and then determining the phase angle between these current and voltage measurements. Another option would be to measure/determine the reactance and impedance in an appropriate manner, and to then determine the phase angle from these values (e.g., the sine of the phase angle being the ratio of the reactance to the impedance).

The phase angle may be determined using an RCL meter or a phase detection circuit (e.g., having an oscillator, multiplexer, filter, phase detection circuit), and may be referred to as a phase module. This phase module (measurement and/or detection) may be disposed at any appropriate location, such as by being incorporated into or embedded in the catheter handle set, by being in the form of a standalone unit between the ablation catheter and the power generator, by being incorporated into or embedded in the power generator, by being incorporated into an electrophysiology or EP mapping system, or by being part of an electrophysiology recording system.

Assessment of the coupling of the electrode with the tissue (step 408 of the protocol 400) may be undertaken in any appropriate manner. For instance, the phase angle determined through step 404 may be compared with one or more benchmark phase angle values (e.g., using a phase angle comparator). These benchmark phase angle values may be determined/set in any appropriate manner, for instance empirically. These benchmark phase angle values may be stored in an appropriate data structure, for instance on a computer-readable data storage medium, or otherwise may be made available to a phase angle comparator. Generally and in one embodiment, the phase angle decreases as more electrode-tissue (e.g., myocardium) coupling exists.

There may be one or more benchmark phase angle values (e.g., a single benchmark phase angle value or a range of benchmark phase angle values) for one or more of the following conditions for purposes of the categorization of step 410 of the assessment protocol 400 of FIG. 9a: 1) insufficient electrode coupling (e.g., an electrode coupling where the associated phase angle being less than "A" is equated with an insufficient electrode coupling); 2) sufficient electrode coupling (e.g., an electrode coupling with an associated phase angle greater than "A" and less than "B" being equated with a sufficient electrode coupling); and 3) elevated or excessive electrode coupling (e.g., an electrode coupling where the associated phase angle being greater than "B" is equated with an elevated or excessive electrode coupling). One embodiment equates the following phase angle values with the noted conditions:

insufficient electrode coupling: $\Phi > -5°$
sufficient electrode coupling: $-5° > \Phi > -10°$
elevated/excessive electrode coupling: $\Phi < -10°$ An "elevated" or "excessive" electrode coupling may be elevated/excessive in relation to the electrical coupling, the mechanical coupling, or both (the coupling between the electrode and the target tissue). In one embodiment, an elevated/excessive or hard electrode coupling means an elevated/excessive mechanical contact between the electrode and the target tissue. It may be desirable to know when an elevated or excessive mechanical contact exists between the electrode and tissue for a variety of reasons. For instance, it may be desirable to avoid an elevated or excessive mechanical contact between the electrode and the target tissue (e.g., to reduce the likelihood of directing the electrode through a tissue wall, membrane, or the like). However, it may also be desirable to know when a sufficient mechanical force is being exerted on the target tissue by the electrode (e.g., to increase the likelihood of directing the electrode through a tissue wall, membrane, or the like to gain access to a desired region on the other side of this tissue wall or membrane).

The result of the assessment of step 408 may be output in any appropriate manner pursuant to step 412 of the electrode coupling assessment protocol 400 of FIG. 9a. Any appropriate output may be utilized, for instance visually (e.g., a bar graph or any other appropriate display at any appropriate location or combination of locations), audibly (e.g., an alarm), physically (e.g., by vibrating a handle being held by a physician that is performing an electrode-based procedure, and as discussed in more detail herein), or any combination thereof. A single output may be provided. A combination of two or more outputs may also be utilized. One or more outputs may be issued to a single location or to multiple locations.

Figure 9B:
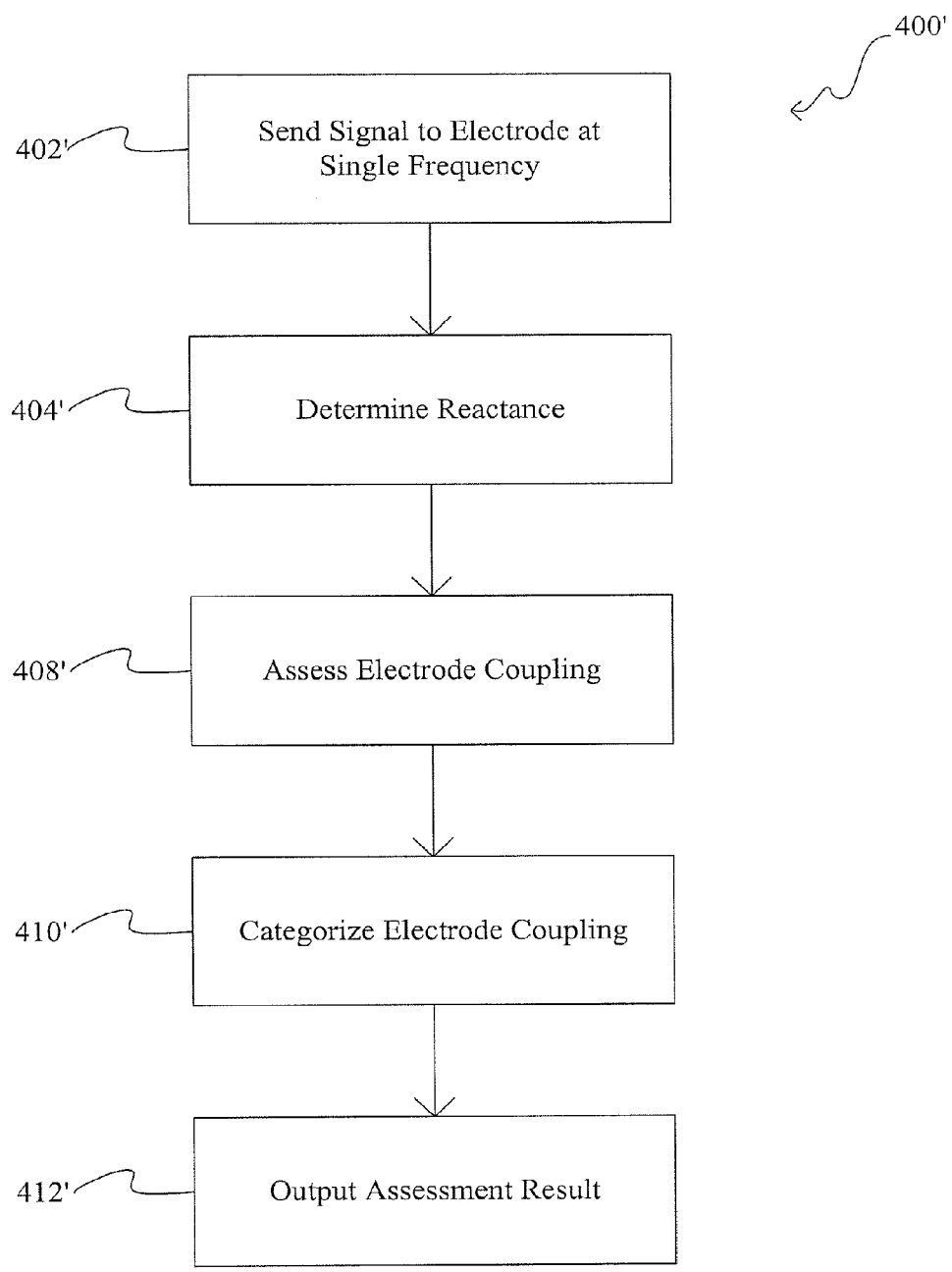
FIG. 9b illustrates one embodiment of a protocol that may be used to assess a coupling between an electrode and tissue based upon a reactance comparison.

FIG. 9b illustrates one embodiment of an electrode coupling assessment protocol 400' that may be used to assess the coupling of an electrode (e.g., a catheter electrode) with any appropriate tissue, where this assessment is reactance based. As the protocol 400' is a variation of the protocol 400 of FIG. 9a, a "single prime" designation is used in relation the reference numerals that identify the individual steps of the protocol 400' of FIG. 9b.

Step 402' of the assessment protocol 400' of FIG. 9b is directed to sending an electrical signal. Only a single frequency is required for the protocol 400' to provide its assessment. That is, the electrode coupling assessment may be provided using a single frequency in the case of the assessment protocol 400'. Typically this will be after the electrode has been positioned at least in the general vicinity of the target tissue (e.g., within a heart chamber). A reactance of the electrical circuit that includes the electrode and the target tissue is thereafter determined at step 404'. This reactance may be determined in any appropriate manner. For instance, the phase angle may be measured (e.g., in accordance with the foregoing), the impedance may be measured, and the reactance may be calculated from these two values (e.g., the sine of the phase angle is equal to the ratio of the reactance to the impedance). Another option for determining the reactance would be to determine the phase or frequency response of a pulse wave.

The electrode coupling is assessed at step 408' of the protocol 400' based upon the above-noted reactance. This electrode coupling from step 408' may be categorized through execution of step 410'. However, the categorization of step 410' may not be required in all instances. In any case, the result of the assessment is output pursuant to step 412'. Step 412' may correspond with step 412 of the electrode coupling assessment protocol 400 of FIG. 9a.

Assessment of the electrode coupling with the tissue (step 408' of the protocol 400') may be undertaken in any appropriate manner. For instance, the reactance determined through step 404' may be compared with one or more benchmark reactance values (e.g., using a reactance comparator). These benchmark reactance values may be determined/set in any appropriate manner, for instance empirically. These benchmark reactance values may be stored in an appropriate data structure, for instance a computer-readable data storage medium, or otherwise may be made available to a reactance comparator. Generally and in one embodiment, the reactance decreases as more electrode-tissue (e.g., myocardium) coupling exists.

There may be one or more benchmark reactance values (e.g., a single benchmark reactance value or a range of benchmark reactance values) for one or more of the following conditions for purposes of the categorization of step 410': 1) insufficient electrode coupling (e.g., an electrode coupling where the associated reactance being less than "A" is equated with insufficient electrode coupling); 2) sufficient electrode coupling (e.g., an electrode coupling with an associated reactance greater than "A" and less than "B" being equated with a sufficient electrode coupling); and 3) elevated or excessive electrode coupling (e.g., an electrode coupling where the associated reactance being greater than "B" is equated with an elevated or excessive electrode coupling). One embodiment equates the following reactance values for the noted conditions:

insufficient electrode coupling: X>−5
sufficient electrode coupling: −5>X>−15
elevated/excessive electrode coupling: X<−15

Figure 9C:
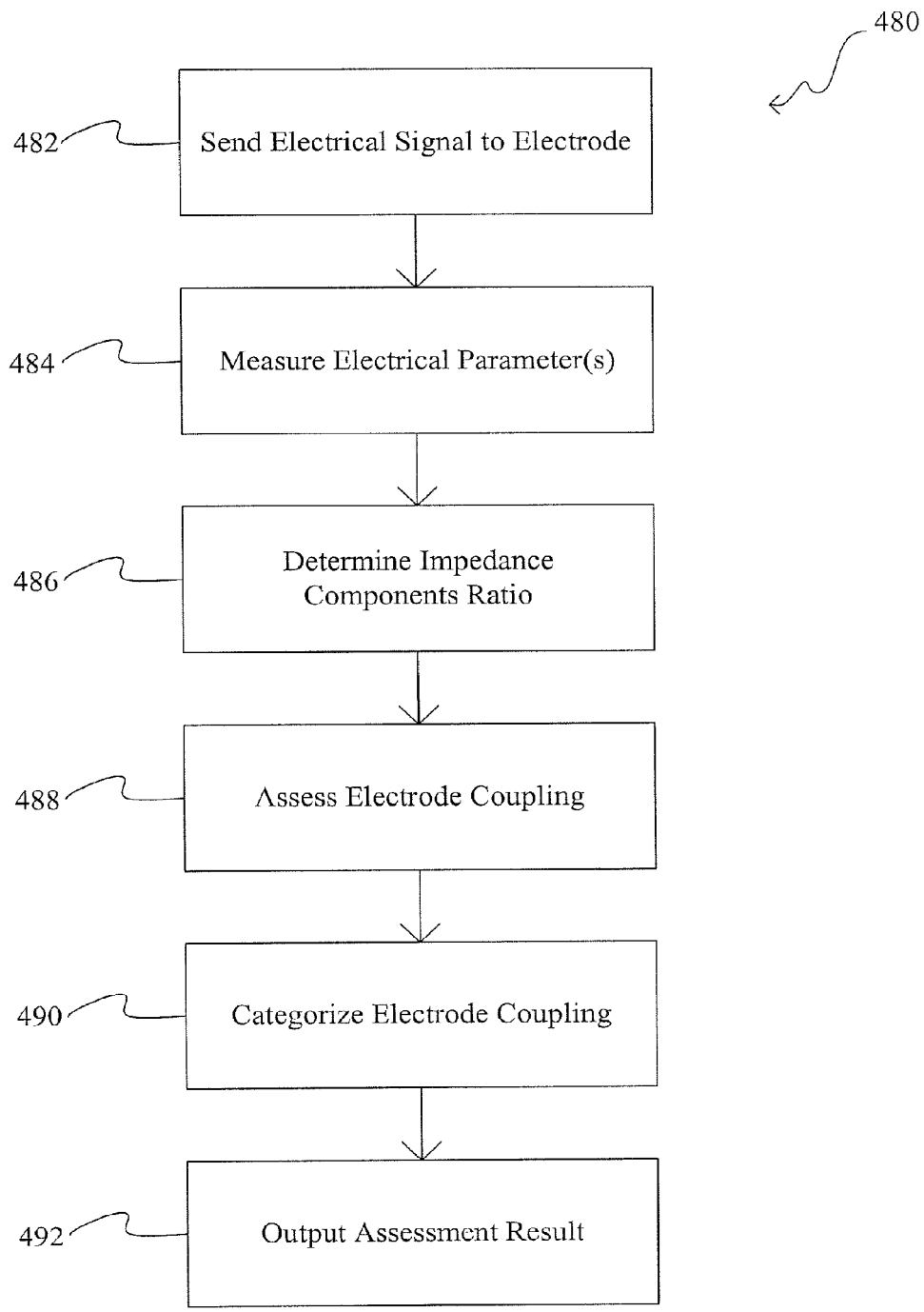
FIG. 9c illustrates one embodiment of a protocol that may be used to assess a coupling between an electrode and tissue based upon an impedance components ratio comparison.

One benefit of basing the electrode coupling assessment upon phase angle is that the phase angle is more insensitive to changes from patient to patient, or operation setup, than both impedance or reactance when considered alone or individually. Other ways of realizing less sensitivity to changes from tissue to tissue or such other conditions may be utilized to provide an electrode coupling assessment. FIG. 9c illustrates such an embodiment of an electrode coupling assessment protocol 480—a protocol 480 that may be used to assess the coupling of an electrode (e.g., a catheter electrode) with any appropriate tissue. Step 482 of the assessment protocol 480 is directed to sending an electrical signal to an electrode at a certain frequency. At least one electrical parameter is measured at step 484. What may be characterized as an "impedance components ratio" is then determined from this measurement at step 486. The phrase "impedance components ratio" means any term that is a ratio of two individual components of the impedance, such as the phase angle (the tangent of the phase angle being equal to the ratio of reactance to resistance). The impedance components ratio may be determined in any appropriate manner, such as by simply measuring a phase angle. Other ways for determining the impedance components ratio include without limitation determining a resistance and reactance at the frequency encompassed by step 482, and calculating the impedance components ratio from these two parameters. Using a ratio of two components that relate to impedance may provide less sensitivity to changes from tissue to tissue for an electrode coupling assessment—an assessment of the coupling between an electrode and the target tissue.

The electrode coupling is assessed at step 488 of the protocol 480. This electrode coupling from step 488 may be categorized through execution of step 490, where step 490 may be in accordance with step 410 of the electrode coupling assessment protocol 400 discussed above in relation to FIG. 9a. As such, the categorization of step 490 may not be required in all instances. In any case, the result of the assessment is output pursuant to step 492. Step 492 may be in accordance step 412 of the electrode coupling assessment protocol 400 discussed above in relation to FIG. 9a.

Figure 10:
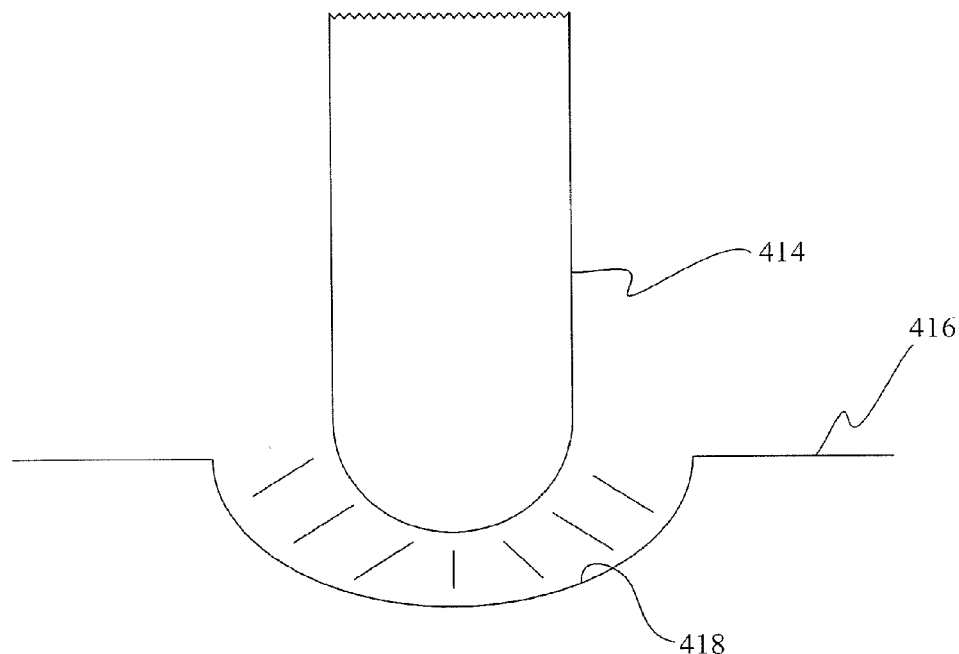
FIG. 10 illustrates a representative, schematic representation of an electrical coupling between an electrode and tissue.

Each of the protocols of FIGS. 9a-c encompasses the electrode coupling being a mechanical coupling between the electrode and the target tissue (i.e., physical contact), as well as an electrical coupling (e.g., a condition when a sufficient portion of the electrical energy passes from the electrode to the target tissue). Any time there is a mechanical coupling, there is an electrical coupling. The reverse, however, is not true. There may be an electrical coupling without the electrode being in contact with the target tissue. FIG. 10 illustrates a representative example of where there is an electrical coupling without having mechanical contact between an electrode 414 and the target tissue 416. Here, the electrode 414 is disposed within a cavity 418 on the surface of the tissue 416, and which provides an electrical coupling between the electrode 414 and the target tissue 416. Therefore, each of the protocols of FIGS. 9a-c may provide an indication of electrical coupling without requiring mechanical contact between the electrode and the target tissue.

Figure 11A:
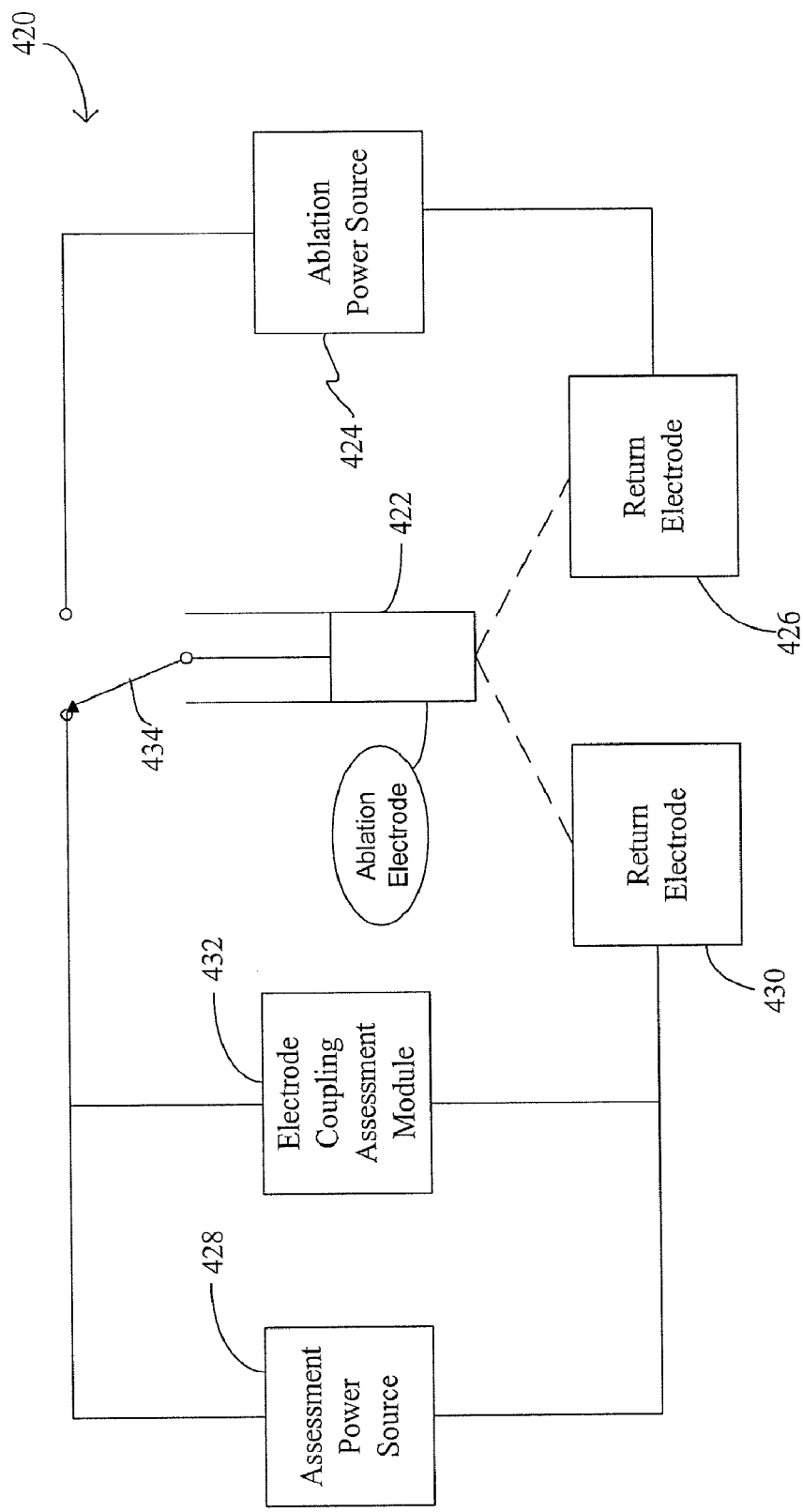
FIG. 11a illustrates a schematic of one embodiment of an ablation system that uses two power sources operating at different frequencies, where only one of these power sources is interconnected with the ablation electrode at any one time, and where one of these power sources is used for assessing a coupling between an electrode and tissue.
Figure 11B:
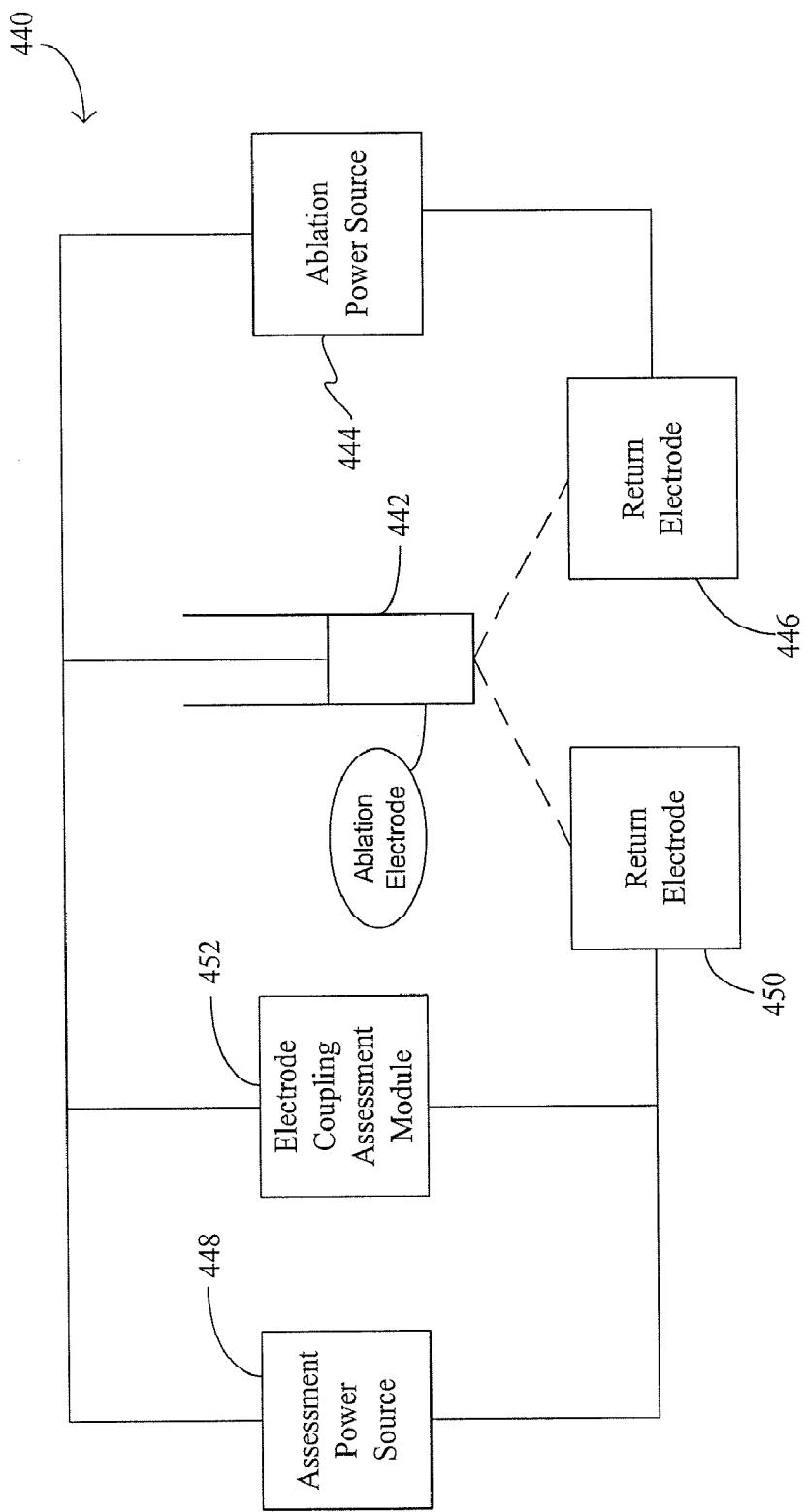
FIG. 11b illustrates a schematic of one embodiment of an ablation system that uses two power sources operating at different frequencies, where both power sources are always interconnected with the ablation electrode, and where one of these power sources is used for assessing a coupling between an electrode and tissue.
Figure 11C:
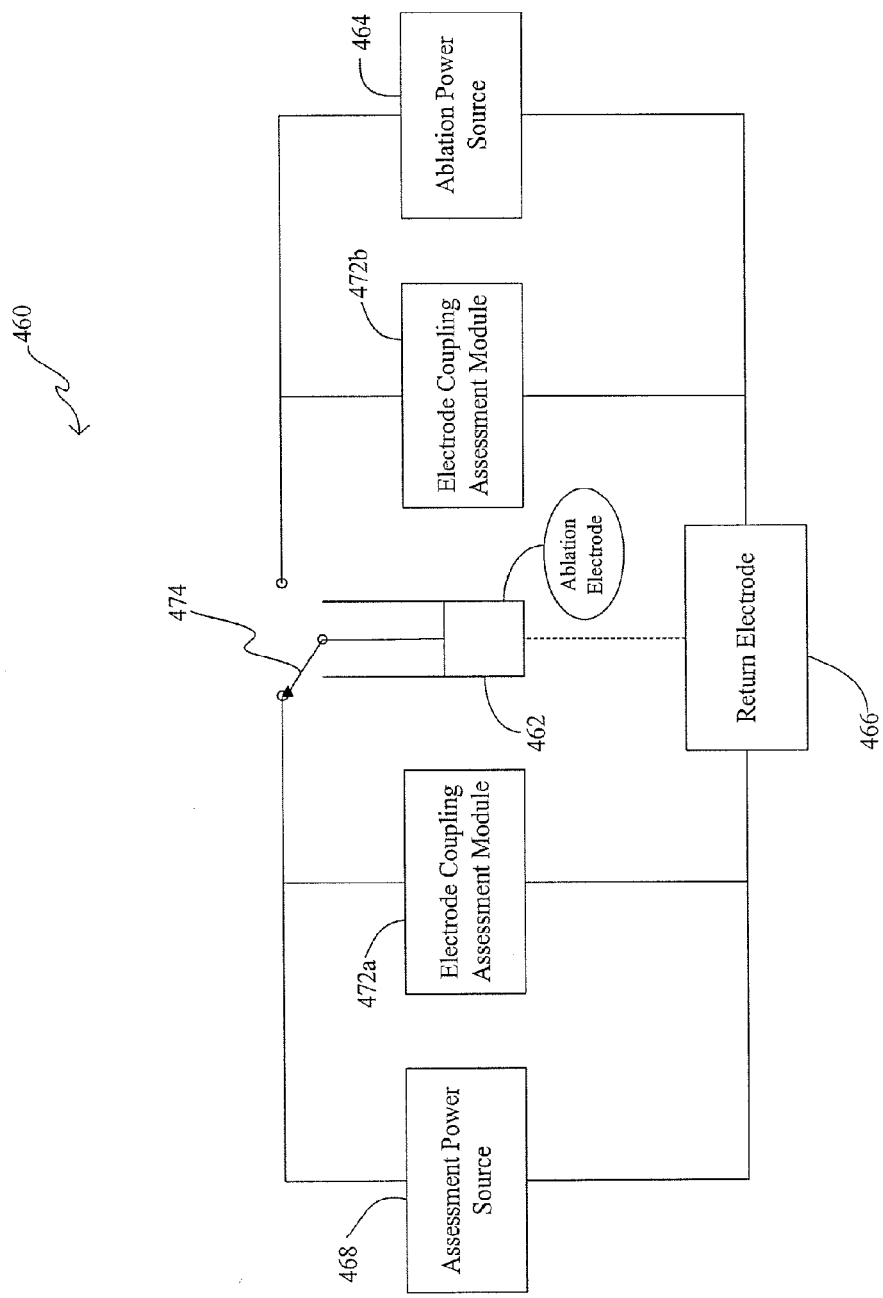
FIG. 11c illustrates a schematic of one embodiment of an ablation system that uses two power sources operating at least generally at the same frequency, where only one of these power sources is interconnected with the ablation electrode at any one time, and where each of these power sources may be used for assessing a coupling between an electrode and tissue.

FIGS. 11a-c schematically present various configurations that may be used in relation to providing an electrode coupling assessment. Although each of these systems will be discussed in relation to an ablation electrode, this electrode coupling assessment may be used for any appropriate application where an electrode provides any appropriate function or combination of functions. Each of the systems of FIGS. 11a-c may be used to provide the assessment protocols discussed above in relation to FIGS. 9a-c. It should also be appreciated that it may be desirable to utilize various other components to commercially implement these configurations, such as filters (e.g., as there may be a current from one or more other sources that should be isolated from the current being used to make the coupling assessment), one or more components to "electrically protect" the patient and/or the electrical circuitry used to make the electrode coupling assessment.

FIG. 11a illustrates an ablation system 420 that includes an ablation power source 424, an ablation electrode 422, and a return electrode 426. Any appropriate frequency may be used by the ablation power source 424. Each of the ablation electrode 422 and return electrode 426 may be of any appropriate size, shape, and/or configuration. Typically the ablation electrode 422 will be in the form of a catheter electrode that is disposed within the patient's body. The return electrode 426 may be disposed at any appropriate location (e.g., a ground patch disposed on the skin of a patient; a catheter electrode disposed within the body of a patient).

Additional components of the ablation system 420 include an electrode coupling assessment power source 428 (hereafter the "assessment power source 428"), an assessment return electrode 430, and an electrode coupling assessment module 432 (hereafter the "assessment module 432"). Any appropriate frequency may be used by the assessment power source 428. Typically, the ablation power source 424 will also use a significantly higher current than the assessment power source 428.

The assessment return electrode 430 may be of any appropriate size, shape, and/or configuration, and may be disposed at any appropriate location. One embodiment has the return electrode 426 and the assessment return electrode 430 being in the form of separate structures that are disposed at different locations. Another embodiment has the functionality of the return electrode 426 and the functionality of the assessment return electrode 430 be provided by a single structure (a single unit that functions as both a return electrode 426 and as an assessment return electrode 430).

The ablation electrode 422 either receives power from the ablation power source 424 or the assessment power source 428, depending upon the position of a switch 434 for the ablation system 420. That is, ablation operations and electrode coupling assessment operations may not be simultaneously conducted in the case of the ablation system 420 of FIG. 11a. During electrode coupling assessment operations, the switch 434 is of course positioned to receive power from the assessment power source 428. This allows the assessment module 432 to assess the coupling between the ablation electrode 422 and the target tissue. Any appropriate configuration may be utilized by the assessment module 432 to provides its electrode coupling assessment function, including without limitation the various configurations addressed herein (e.g., assessment based upon phase angle comparisons; assessment based upon reactance comparisons; assessment based upon impedance components ratio comparisons; assessment based upon identifying the frequency associated with a 0° phase frequency or a 0 inductance frequency as will be discussed below in relation to FIGS. 12a-b). The assessment module 432 may provide the electrode coupling assessment using any of the protocols of FIGS. 9a-c from a single frequency.

FIG. 11b illustrates an ablation system 440 that includes an ablation power source 444, an ablation electrode 442, and a return electrode 446. Any appropriate frequency may be used by the ablation power source 444. Each of the ablation electrode 442 and return electrode 446 may be of any appropriate size, shape, and/or configuration. Typically the ablation electrode 442 will be in the form of a catheter electrode that is disposed within the patient's body. The return electrode 446 may be disposed at any appropriate location (e.g., a ground patch disposed on the skin of a patient; a catheter electrode disposed within the body of a patient).

Additional components of the ablation system 440 include an electrode coupling assessment power source 448 (hereafter the "assessment power source 448"), an assessment return electrode 450, and an electrode coupling assessment module 452 (hereafter the "assessment module 452"). Any appropriate frequency may be used by the assessment power source 448. However, the ablation power source 444 and the assessment power source 448 operate at different frequencies in the case of the ablation system 440 in order to accommodate the simultaneous execution of ablation and electrode coupling assessment operations. Moreover, typically the ablation power source 444 will also use a significantly higher current than the assessment power source 448.

The assessment return electrode 450 may be of any appropriate size, shape, and/or configuration, and may be disposed at any appropriate location. One embodiment has the return electrode 446 and the assessment return electrode 450 being in the form of separate structures that are disposed at different locations. Another embodiment has the functionality of the return electrode 446 and the functionality of the assessment return electrode 450 be provided by a single structure (a single unit that functions as both a return electrode 446 and as an assessment return electrode 450).

The ablation electrode 442 may simultaneously receive power from the ablation power source 444 and the assessment power source 448. That is, ablation operations and electrode coupling assessment operations may be simultaneously executed in the case of the ablation system 440 of FIG. 11b. In this regard, the ablation power source 444 and the assessment power source 448 again will operate at different frequencies. The assessment module 452 may provide the electrode coupling assessment using any of the protocols of FIGS. 9a-c from a single frequency. In any case, the assessment module 452 assesses the coupling between the ablation electrode 442 and the target tissue. The discussion presented above with regard to the assessment module 432 for the ablation system 420 of FIG. 11a is equally applicable to the assessment module 452 for the ablation system 440 of FIG. 11b.

FIG. 11c illustrates an ablation system 460 that includes an ablation power source 464, an ablation electrode 462, and a return electrode 466. Any appropriate frequency may be used by the ablation power source 464. Each of the ablation electrode 462 and return electrode 466 may be of any appropriate size, shape, and/or configuration. Typically the ablation electrode 462 will be in the form of a catheter electrode that is disposed within the patient's body. The return electrode 466 may be disposed at any appropriate location (e.g., a ground patch disposed on the skin of a patient; a catheter electrode disposed within the body of a patient).

Additional components of the ablation system 460 include an electrode coupling assessment power source 468 (hereafter the "assessment power source 468"). Any appropriate frequency may be used by the assessment power source 468. Typically, the ablation power source 464 will also use a significantly higher current than the assessment power source 468.

The ablation system 460 further includes a pair of electrode coupling assessment modules 472a, 472b (hereafter the "assessment module 472a" and "the assessment module 472b"). The assessment module 472a is associated with the assessment power source 468, while the assessment module 472b is associated with the ablation power source 464. Both ablation operations and electrode coupling assessment operations utilize the return electrode 466 in the illustrated embodiment, although it may be possible to utilize separate return electrodes as in the case of the embodiments of FIGS. 11a and 11b discussed above.

The ablation electrode 462 either receives power from the ablation power source 464 or the assessment power source 468, depending upon the position of a switch 474 for the ablation system 460. However, electrode coupling assessment operations may be executed regardless of the position of the switch 474, unlike the embodiment of FIG. 11a. When the ablation electrode 462 is electrically interconnected with the assessment power source 468 through the switch 474, the assessment module 472a is used to assess the coupling between the ablation electrode 462 and the target tissue. When the ablation electrode 462 is electrically interconnected with the ablation power source 464 through the switch 474, the assessment module 472b is used to assess the coupling between the ablation electrode 462 and the target tissue. The assessment modules 427a, 472b may each provide an electrode coupling assessment using any of the protocols of FIGS. 9a-c from a single frequency.

Any appropriate configuration may be utilized by each of the assessment module 472a, 472b to provide their respective electrode coupling assessment functions, including without limitation the various configurations addressed herein. The discussion presented above with regard to the assessment module 432 for the ablation system 420 of FIG. 11a is equally applicable to the assessment modules 472a, 472b for the ablation system 460 of FIG. 11c. Typically, the assessment modules 472a, 472b will be of the same configuration for assessing electrode coupling, although such may not be required in all instances. When the assessment modules 472a, 472b are the same configuration, the ablation power source 464 and the assessment power source 468 will typically operate at the same frequency. Therefore, the ablation system 460 accommodates the assessment of electrode coupling prior to initiating ablation operations (e.g., using an assessment current and the assessment module 472a), and further accommodates the assessment of electrode coupling during ablation operations (e.g., using the actual ablation current versus a smaller current, and using the assessment module 472b). The ablation system 440 of FIG. 11b also accommodates the assessment of electrode coupling during ablation operations, but it uses a separate assessment current versus the actual ablation current.

One of the electrodes used by the assessment module in each of the embodiments of FIGS. 11a-c is of course the ablation or "active" electrode. Both the electrode coupling assessment module and the ablation electrode need another electrode that interfaces with the patient in some manner to provide their respective functions. FIG. 1a illustrates one embodiment where the return electrode used by the assessment module and the return electrode that cooperates with the ablation electrode to provide electrical energy to the tissue for providing one or more desired functions are integrated into a common structure. More specifically, an ablation electrode 20 (e.g., a catheter electrode) is disposed in a chamber of the heart 16 (e.g., the left atrium), and is in the form of a catheter electrode 20. A return electrode 20a (e.g., a catheter electrode) is also disposed in the same chamber of the heart 16 and may be used by each of the assessment modules of FIGS. 11a-c (to assess coupling of the ablation electrode 20 with the target tissue 24) and the ablation electrode 20 (to deliver electrical energy to the target tissue 24 to provide a desired medical function). Therefore, the ablation electrode 20 and the return electrode 20a may be associated with different catheters, and thereby may be independently moved or manipulated. In one embodiment, the return electrode 20a has a larger surface area than the ablation electrode 20. Each of the ablation electrode 20 and the return electrode 20a have electrode tips that are spaced from each other.

The configuration shown in FIG. 1a provides two electrodes 20, 20a in a common heart chamber. Another option would be to have two or more electrodes be associated with a common catheter, but where the catheter has two separated distal portions each with an electrode on a separate electrode tip on a distal end thereof such that the electrode tips are spaced from each other.

Figure 12A:
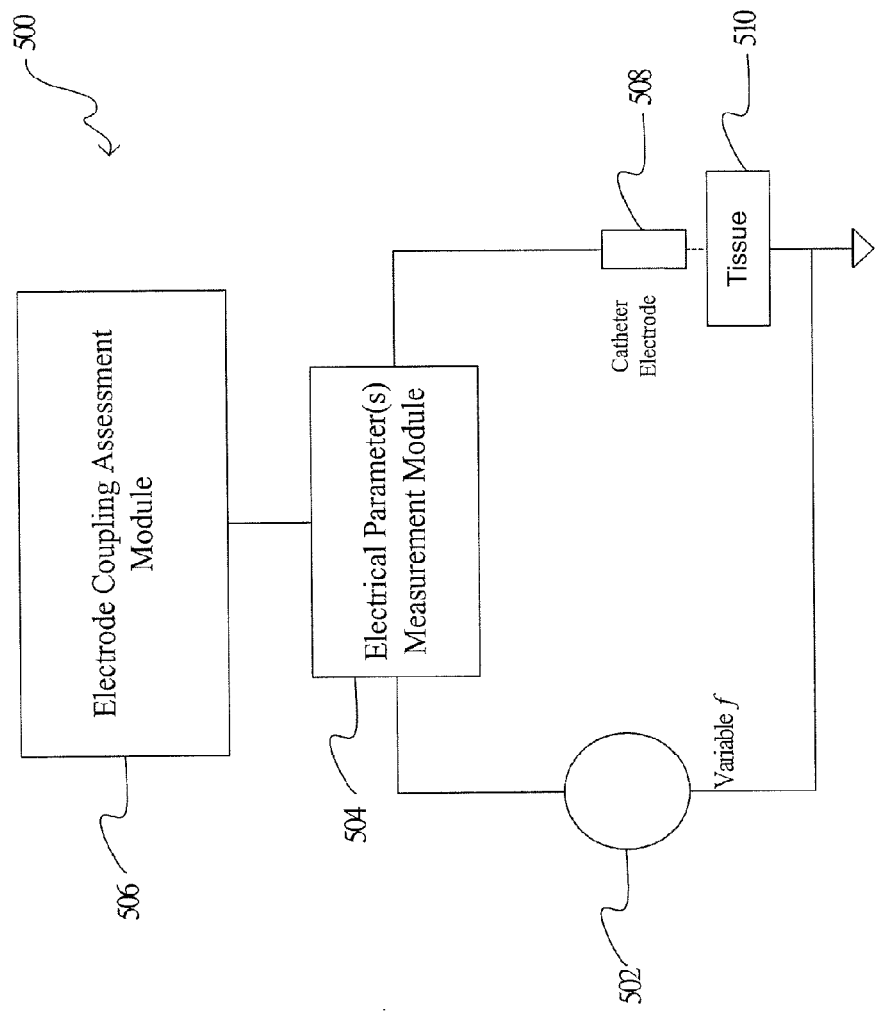
FIG. 12a illustrates one embodiment of a system for assessing a coupling between an electrode and tissue.
Figure 12B:
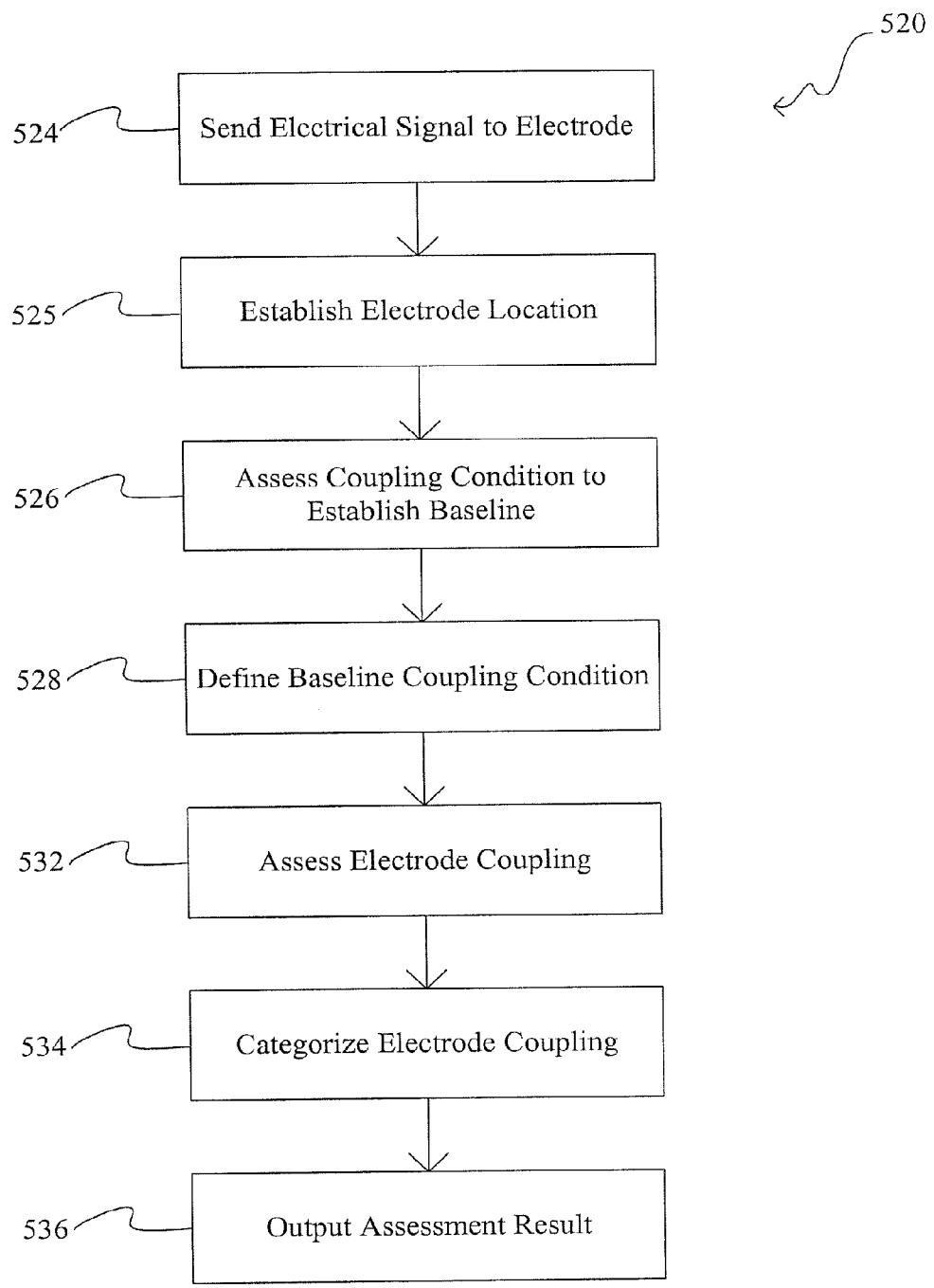
FIG. 12b illustrates one embodiment of a protocol that may be used to assess a coupling between an electrode and tissue based upon identifying a baseline coupling condition.

One or more ways of using a phase angle to assess the coupling between an active electrode and the target tissue have been presented above. Another way in which a phase angle may be used to assess electrode coupling is illustrated in FIGS. 12a-b. FIG. 12a presents a schematic of an electrode coupling assessment system 500 which includes a variable frequency source 502, an electrical parameter measurement module 504, an electrode coupling assessment module 506, and an electrode 508 that is to be coupled with tissue 510 to provide a desired function or combination of functions (e.g., ablation). The return electrode is not illustrated in FIG. 12a, but may be of any appropriate type and disposed at any appropriate location. Generally, the variable frequency source 502 provides an electrical signal to the electrode 508 for purposes of transmitting electrical energy to the tissue 510. The electrical parameter measurement module 504 may be of any appropriate type and/or configuration, measures one or more electrical parameters, and provides information used by the electrode coupling assessment module 506. The electrode coupling assessment module 506 assesses the coupling between the electrode 508 and the tissue 510.

FIG. 12b presents one embodiment of an electrode coupling protocol 520 that may be used by the electrode coupling assessment module 506 of FIG. 12a. One or more electrical signals are sent to the electrode 508 through execution of step 524. A baseline coupling condition can be assessed. For example, the baseline coupling condition can be defined pursuant to steps 524-528 of protocol 520. The term "baseline coupling condition" encompasses a zeroed phase angle or zeroed reactance at a desired frequency in a medium (e.g., blood).

A determination is made through execution of step 525 to determine when the electrode is in the desired medium, e.g., the blood. Next, through the execution of step 526, the baseline coupling condition is established. For example, the physician can activate an input device to indicate the establishment of the baseline coupling condition. Then protocol 520 adjusts to the baseline coupling condition in step 528 by correcting the phase angle or the reactance to zero.

In an alternative to zeroing the baseline coupling condition, the value(s) of the baseline coupling condition established in step 526 may be stored and used to determine an electrode coupling condition relative to such a baseline coupling condition.

In a second alternative, the baseline coupling condition may be determined by comparing the determined phase angle with one or more predetermined benchmark values. These benchmark values may be determined/set in any appropriate manner, for instance empirically through in vitro, ex vivo, or in vivo studies. These benchmark values may be stored in an appropriate data structure, for instance on a computer-readable data storage medium, or otherwise may be made available to a phase comparator.

The electrode coupling may be assessed pursuant to step 532 of the protocol 520 using the baseline coupling condition from step 528. One or more electrical parameters may be determined in any appropriate manner and compared with the corresponding value of the baseline coupling condition from step 528. For instance, the following categories may be provided: 1) insufficient electrode coupling (e.g., an electrode coupling where the value(s) associated with a baseline coupling condition being less than "A" is equated with insufficient electrode coupling); 2) sufficient electrode coupling (e.g., an electrode coupling where the value(s) associated with a baseline coupling condition greater than "A" and less than "B" is equated with a sufficient electrode coupling); and 3) elevated or excessive electrode coupling (e.g., an electrode coupling where the value(s) associated with a baseline coupling condition being greater than "B" is equated with an elevated or excessive electrode coupling).

Figure 12C:
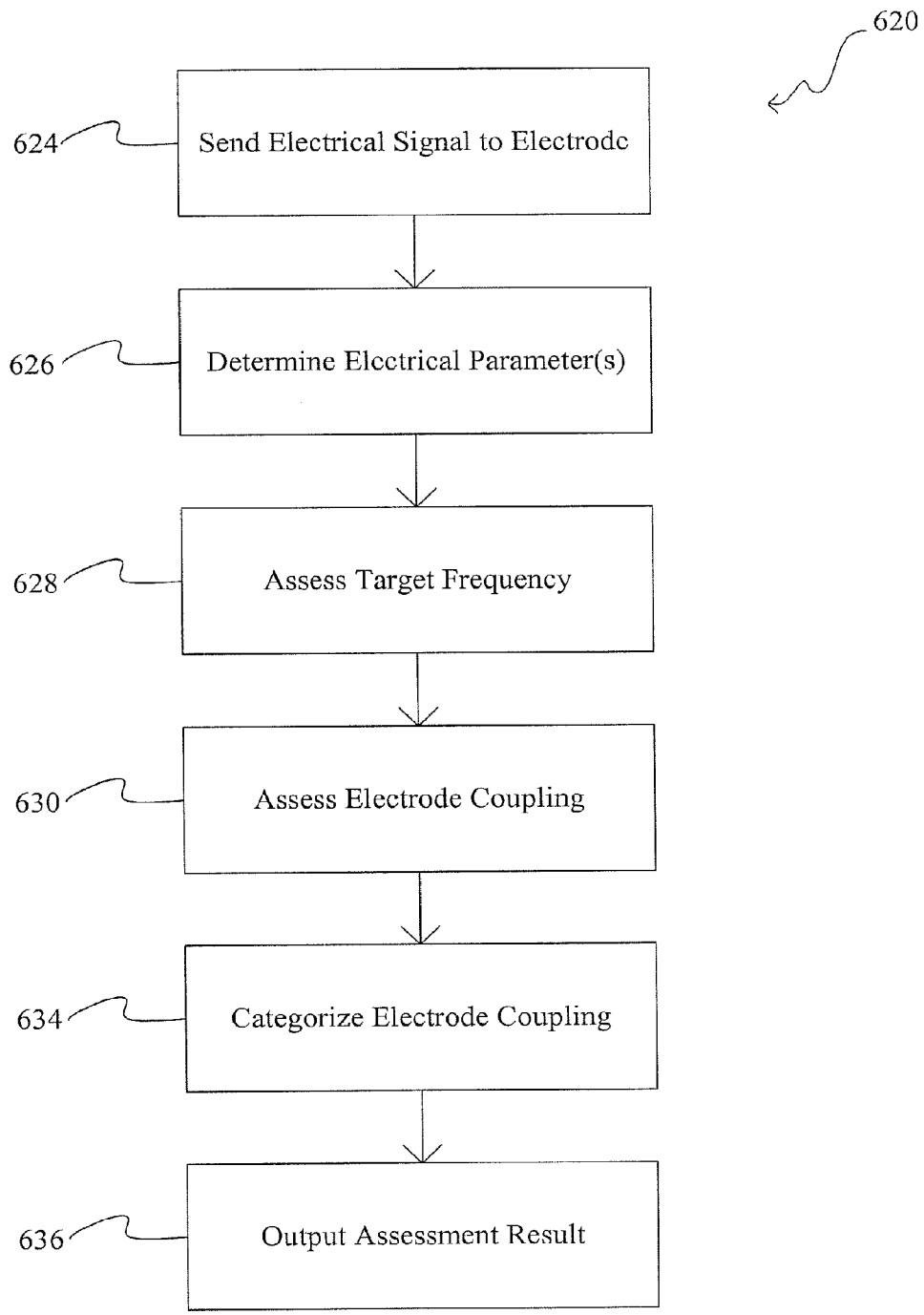
FIG. 12c illustrates one embodiment of a protocol that may be used to assess a coupling between an electrode and tissue based upon identifying a target frequency.

In another embodiment, the electrical coupling is measured as a function of a "target frequency"—a frequency that corresponds to a preset value for an electrical parameter (e.g., a preset reactance or a phase angle value). FIG. 12c presents one embodiment of an electrode coupling protocol 620 that may be used by the electrode coupling assessment module 506 of FIG. 12a. Electrical signals are sent to the electrode 508 through execution of step 624. The electrical signals are sent at varying frequencies. At each frequency sent, step 626 measures the reactance and/or phase. Step 628 compares the measured reactance or phase with a preset value. The frequency at which the reactance or phase matches the preset value is the "target frequency." Any appropriate value may be used for the preset value for purposes of step 628, including a positive value, zero, or a negative value (e.g., a zero phase angle, such that the target frequency may be referred to as a 0° phase frequency; or a zero inductance, such that the target condition frequency may be referred to as a 0 inductance frequency).

When the protocol 620 determines that the target frequency exists, the protocol 620 proceeds to step 630 where the coupling of the electrode 508 with the tissue 510 is assessed using the information provided by step 628, and the result of this assessment is output pursuant to step 636 of the protocol 620.

Step 636 may be in accordance with step 412 of the protocol discussed above in relation to FIG. 9a.

Assessment of the electrode coupling with the tissue is provided through step 630 of the protocol 620 of FIG. 12c. The target frequency from step 628 may be compared with one or more benchmark frequency values (e.g., using a comparator). These benchmark frequency values may be determined/set in any appropriate manner. The values can be predetermined, for instance empirically through in vitro, ex vivo, or in vivo studies. These benchmark frequency values may be stored in an appropriate data structure, for instance on a computer-readable data storage medium. The benchmark frequency values can also be determined during the procedure by a physician. For example, a determination can be made when the electrode is in the desired medium, e.g., the blood. At that point the physician can activate an input device to set the benchmark value for the existing coupling relevant condition.

There may be one or more benchmark frequency values (e.g., a single benchmark frequency value or a range of benchmark frequency values) for one or more of the following conditions for purposes of the categorization for the assessment protocol 620 of FIG. 12c: 1) insufficient electrode coupling (e.g., an electrode coupling where the target frequency being less than "A" is equated with insufficient electrode coupling); 2) sufficient electrode coupling (e.g., an electrode coupling where the target frequency is greater than "A" and less than "B" is equated with sufficient electrode coupling); and 3) excessive electrode coupling (e.g., an electrode coupling where the target frequency being greater than "B" is equated with an excessive electrode coupling). One embodiment equates the following target frequency values for the noted conditions (where $F_t$ is the target frequency for the noted condition):

insufficient electrode coupling: $F_t < 120$ kHz
sufficient electrode coupling: $120$ kHz $< F_t < 400$ kHz
elevated/excessive electrode coupling: $F_t > 400$ kHz The protocol 620 of FIG. 12c may be implemented in any appropriate manner. For instance, the impedance may be monitored to obtain the target phase frequency by sweeping the signal frequency (e.g., in accordance with the system 500 of FIG. 12a). This frequency sweep could be provided between two appropriate values (e.g., 50 kHz and 1 MHz) and using any appropriate incremental change between these values for the sweep (e.g., 10-20 kHz increments). This approach uses what may be referred to as frequency switching, which involves measuring the impedance one frequency at a time and rotating the frequencies by a frequency synthesizer or the like. Another approach would be to combine multiple frequencies together, and to determine the impedance at each of the individual frequencies from the combined signal through filtering. It should be appreciated that it may be such that interpolation will be required to determine the frequency associated with the target frequency condition in some cases (e.g., where the frequency associated with the target frequency condition is determined to exist between two frequencies used by the protocol 620).

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. It is intended that all matter contained in the above description or shown in the accompanying drawings shall be interpreted as illustrative only and not limiting. Changes in detail or structure may be made without departing from the spirit of the invention as defined in the appended claims.

What is claimed:

1. A medical system comprising
   a first electrical power source configured to provide a first current to an electrode for executing a first medical procedure; and
   a first electrode coupling assessment module, wherein said first electrode coupling assessment module is configured to assess a coupling between the electrode and a target tissue associated with said first medical procedure, and wherein said first electrode coupling assessment module uses said first current to assess said coupling;
   second electrical power source configured to provide a second current to the electrode for executing an electrode coupling assessment operation; and
   a second electrode coupling assessment module, wherein said second electrode coupling assessment module is configured to assess a coupling between the electrode and the target tissue, and wherein said second electrode coupling assessment module uses said second current.

2. The medical system of claim 1, further comprising;
   a switch operable to interconnect the electrode with said first electrical power source in a first switch position, and operable to interconnect the electrode with said second electrical power source in a second switch position.

3. The medical system of claim 1, wherein said second current is of a different magnitude than said first current, and wherein a frequency of electrical signals provided by said first and second electrical power sources at said first and second currents, respectively, are substantially equal.

4. A medical system comprising:
   a first electrical power source configured to provide a first current to an electrode for executing a first medical procedure;
   a first electrode coupling assessment module, wherein said first electrode coupling assessment module is configured to assess a coupling between the electrode and a target tissue associated with said first medical procedure, and wherein said first electrode coupling assessment module uses said first current to assess said coupling;
   a second electrical power source configured to provide a second current to the electrode for executing an electrode coupling assessment operation;
   a switch operable to interconnect said electrode with said first electrical power source in a first switch position, and operable to interconnect said electrode with said second electrical power source in a second switch position; and
   a second electrode coupling assessment module, wherein said second electrode coupling assessment module is configured to assess a coupling between the electrode and the target tissue, and wherein said second electrode coupling assessment module uses said second current.

5. The medical system of claim 4, wherein said second current is of a different magnitude than said first current, and wherein a frequency of electrical signals provided by said first and second electrical power sources at said first and second currents, respectively, are substantially equal.

6. The medical system of claim 4, wherein said first and second electrode coupling assessment modules are of an identical configuration.

7. The medical system of claim 4, wherein said first electrode coupling assessment module is available for assessing said coupling during said first medical procedure, and wherein said second electrode coupling assessment module is available for assessing said coupling only other than during execution of said first medical procedure.

* * * * *